(12) United States Patent
Grenier et al.

(10) Patent No.: US 12,102,517 B2
(45) Date of Patent: Oct. 1, 2024

(54) ABSORBENT ARTICLE COMPRISING A LOWER ACQUISITION AND DISTRIBUTION SYSTEM

(71) Applicant: The Procter & Gamble Company, Cincinnati, OH (US)

(72) Inventors: Adrien Grenier, Frankfurt am Main (DE); Aniruddha Chatterjee, Kelkheim (DE); Behzad Mohebbi, Schwalbach am Taunus (DE)

(73) Assignee: The Procter & Gamble Company, Cincinnati, OH (US)

( * ) Notice: Subject to any disclaimer, the term of this patent is extended or adjusted under 35 U.S.C. 154(b) by 968 days.

(21) Appl. No.: 17/113,276

(22) Filed: Dec. 7, 2020

(65) Prior Publication Data

US 2021/0177672 A1    Jun. 17, 2021

(30) Foreign Application Priority Data

Dec. 11, 2019   (EP) .................................... 19215345

(51) Int. Cl.
  *A61F 13/537*    (2006.01)
  *A61F 13/511*    (2006.01)
  (Continued)

(52) U.S. Cl.
  CPC .................. *A61F 13/53747* (2013.01); *A61F 13/51104* (2013.01); *A61F 13/51401* (2013.01);
  (Continued)

(58) Field of Classification Search
  CPC .......... A61F 13/51458; A61F 13/53704; A61F 13/53747; A61F 13/53756; A61F 13/5376;
  (Continued)

(56) References Cited

U.S. PATENT DOCUMENTS 5,817,081 A   10/1998  Young
6,958,431 B2  10/2005  Fields et al.
(Continued)

FOREIGN PATENT DOCUMENTS

CN    101410078 A    4/2009
CN    101583330 A    11/2009
(Continued)

OTHER PUBLICATIONS

International Search Report and Written Opinion; Application Ser. No. PCT/US2020/063543; dated Mar. 24, 2021, 16 pages.
European Search Report.

*Primary Examiner* — Catharine L Anderson
(74) *Attorney, Agent, or Firm* — Christian M. Best

(57) ABSTRACT

An absorbent article comprising a topsheet, a backsheet, and a layer of absorbent material interposed between the topsheet and the backsheet, wherein the layer of absorbent material (28) comprises superabsorbent polymer. The absorbent article further comprises a lower acquisition and distribution system with at least one nonwoven or woven layer, the lower acquisition and distribution system being interposed between the layer of absorbent material and the backsheet. The absorbent article has a first zone corresponding to 800 μm starting from and including the topsheet and extending towards the backsheet, and a second zone corresponding to 800 μm starting from and including the backsheet and extending towards the topsheet. The amount of liquid in the first and second zone is very small as measured by the NMR test method set out herein.

23 Claims, 17 Drawing Sheets

(51) Int. Cl.
*A61F 13/514* (2006.01)
*A61F 13/15* (2006.01)
*A61F 13/53* (2006.01)
*A61F 13/534* (2006.01)

(52) U.S. Cl.
CPC .. *A61F 13/51458* (2013.01); *A61F 13/53704* (2013.01); *A61F 13/53756* (2013.01); *A61F 13/5376* (2013.01); *A61F 2013/15471* (2013.01); *A61F 2013/15552* (2013.01); *A61F 2013/15861* (2013.01); *A61F 2013/51447* (2013.01); *A61F 2013/530167* (2013.01); *A61F 2013/53062* (2013.01); *A61F 2013/530715* (2013.01); *A61F 2013/53445* (2013.01); *A61F 2013/53454* (2013.01); *A61F 2013/53721* (2013.01); *A61F 2013/53765* (2013.01)

(58) Field of Classification Search
CPC ............ A51F 2013/15471; A51F 2013/15552; A51F 2013/53062; A51F 2013/530715; A51F 2013/53445; A51F 2013/53721; A51F 2013/53765

See application file for complete search history.

(56) References Cited

U.S. PATENT DOCUMENTS

| | | | |
|---|---|---|---|
| 7,258,758 B2 * | 8/2007 | Collier, IV | D04H 1/50 |
| | | | 156/181 |
| 8,426,671 B2 * | 4/2013 | Steffen | A61L 15/24 |
| | | | 604/367 |
| 2004/0127873 A1 | 7/2004 | Varona et al. | |
| 2012/0238981 A1 * | 9/2012 | Weisman | A61F 13/53708 |
| | | | 604/370 |
| 2014/0005622 A1 | 1/2014 | Wirtz | |
| 2017/0135869 A1 | 5/2017 | Moriya et al. | |
| 2018/0303682 A1 | 10/2018 | Nebigil | |
| 2019/0328587 A1 | 10/2019 | Saevecke et al. | |
| 2019/0358097 A1 | 11/2019 | Chmielewski et al. | |
| 2019/0374397 A1 | 12/2019 | Tally et al. | |
| 2021/0401637 A1 | 12/2021 | Tally et al. | |

FOREIGN PATENT DOCUMENTS

| | | |
|---|---|---|
| CN | 109310554 A | 2/2019 |
| EP | 1842513 | 10/2007 |
| WO | 9724095 A1 | 7/1997 |
| WO | 2014200794 A1 | 12/2014 |
| WO | 2015046161 A1 | 4/2015 |
| WO | WO 2018/004564 | 1/2018 |

* cited by examiner

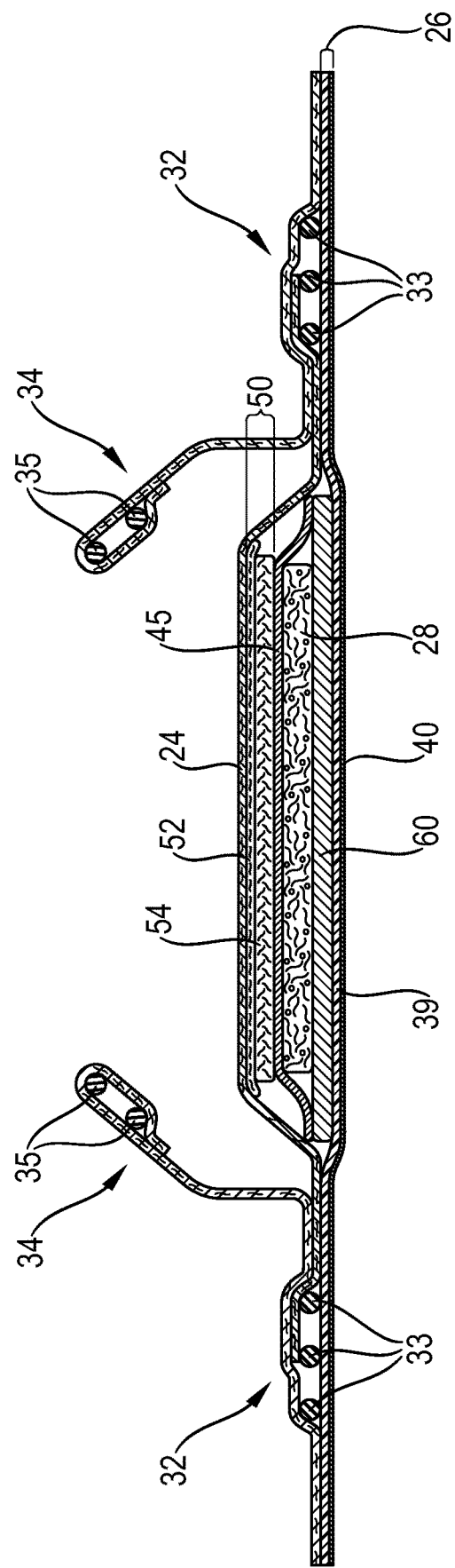

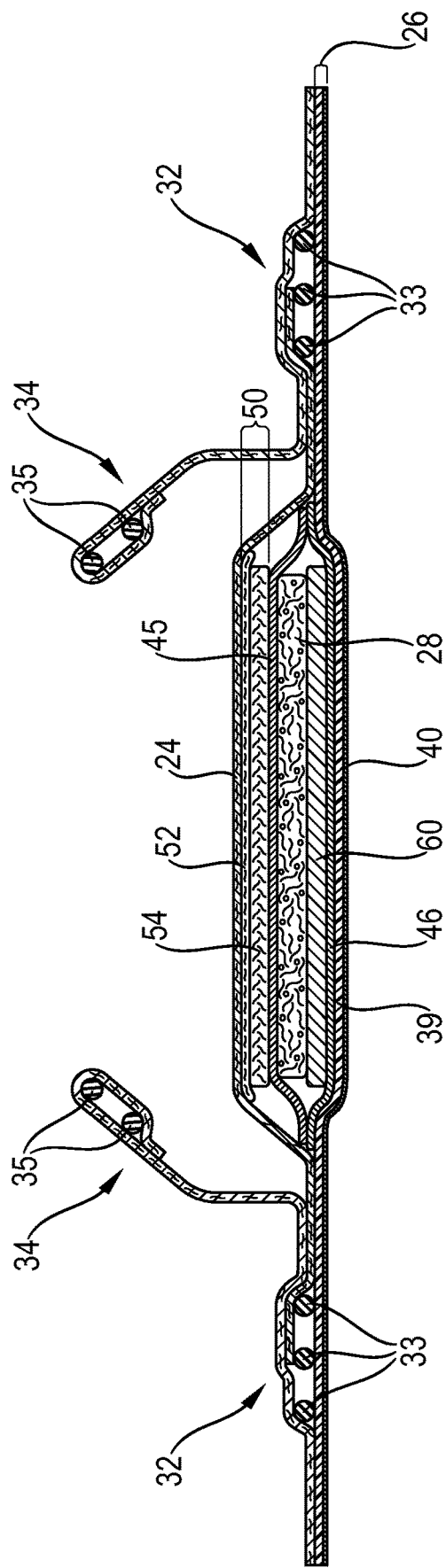

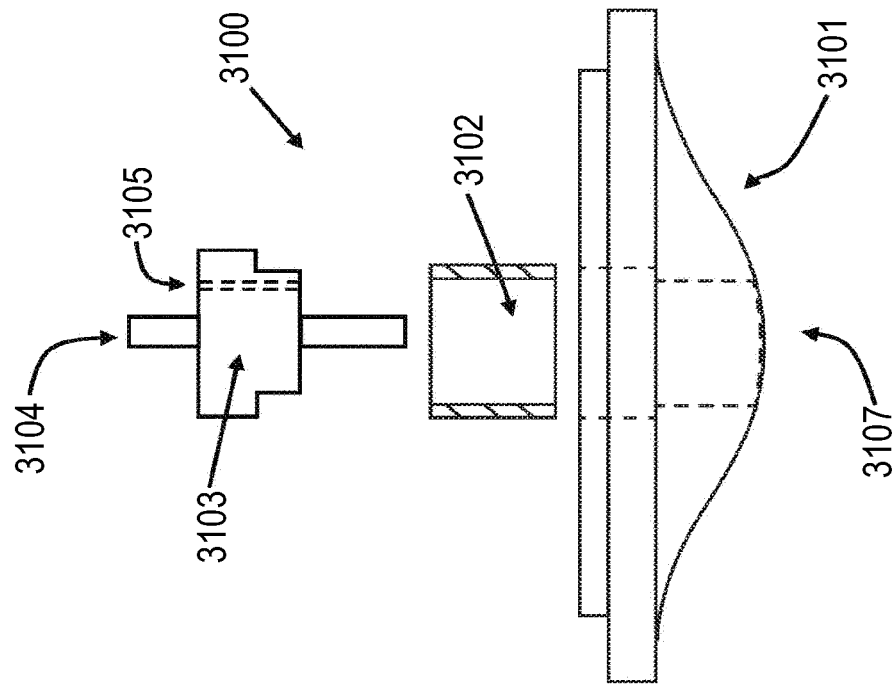
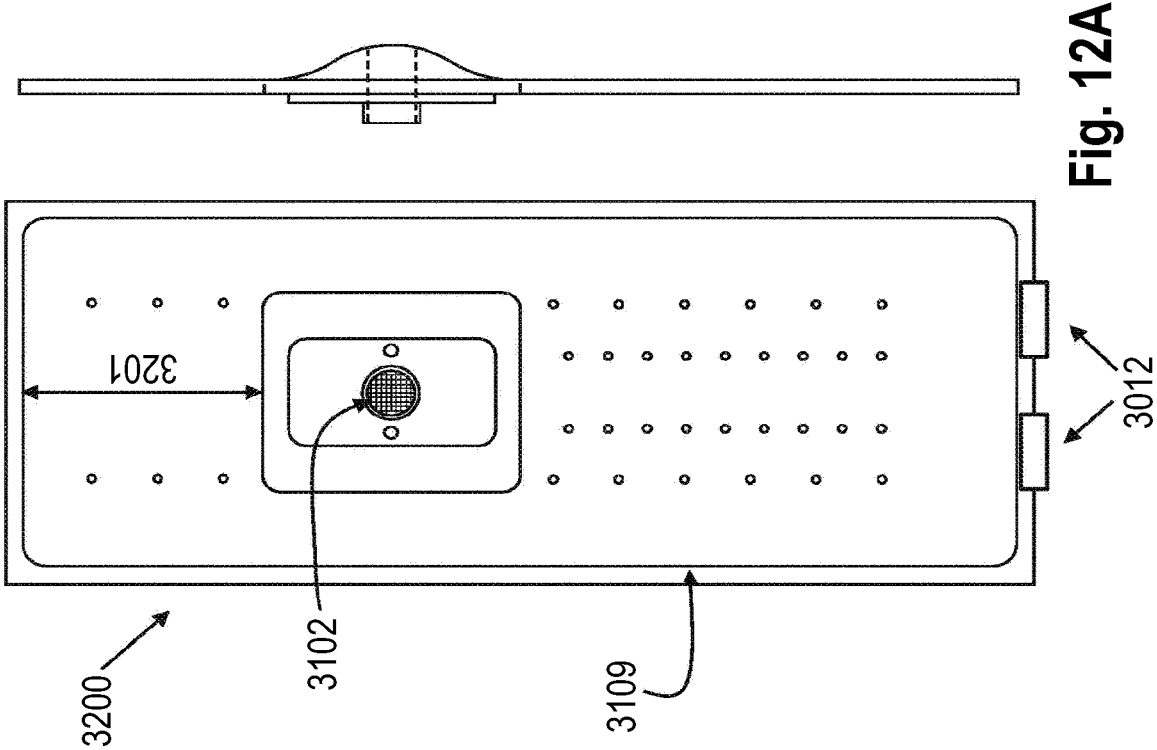
Fig. 12A
Fig. 12B

ABSORBENT ARTICLE COMPRISING A LOWER ACQUISITION AND DISTRIBUTION SYSTEM

CROSS REFERENCE TO RELATED APPLICATION

This application claims priority under 35 U.S.C. § 119 to European Patent Application Serial No. 19215345.0, filed on Dec. 11, 2019, the entire disclosure of which is hereby incorporated by reference.

FIELD OF THE INVENTION

The invention provides an absorbent article for personal hygiene, such as a diaper or pant (for babies, toddlers or adults). The absorbent article comprises a lower acquisition and distribution system between a backsheet and a layer of absorbent material, and, optionally, an upper acquisition and distribution system between a topsheet and the layer of absorbent material. The absorbent article has only minor amounts of liquid in the areas adjacent to the topsheet and adjacent to the backsheet, as measured according to the nuclear magnetic resonance (NMR)-based test method set out herein.

BACKGROUND OF THE INVENTION

Absorbent articles for babies, toddlers and adults are well known and widely used. Absorbent articles, such as diapers and pants, typically have a topsheet and a backsheet with an absorbent core provided in between. Body liquids, such as urine, are disposed into the absorbent article through the topsheet and ultimately absorbed into and stored in the absorbent material of the absorbent core. Typical absorbent materials are cellulose fibers (in the context of absorbent articles also often referred to as "fluff pulp" or "airfelt"), absorbent foams, absorbent synthetic fibers or superabsorbent materials. Commonly used superabsorbent materials are superabsorbent polymers which are typically provided as particles but may also take the form of superabsorbent polymer fibers or superabsorbent polymer foams.

Often, additional acquisition and distribution systems (hereinafter referred to as "ADS") are provided in between the absorbent core and the topsheet. Such systems may be made of one or more layers of materials. For example, an ADS may have an acquisition layer in direct contact with the topsheet, which predominantly serves fast acquisition of fluid from the topsheet to avoid free liquid on the topsheet that can lead to leakage. An additional layer may be applied (the distribution layer) underneath and in direct contact with the acquisition layer. The distribution layer may predominantly serve distribution of fluid within the plane of the layer to provide a more even distribution of liquid throughout the absorbent article. The distribution layer may be in direct contact with the absorbent core. Both layers also serve as a reservoir to temporarily hold liquid before it is ultimately stored in the absorbent core. Alternatively, the ADS may be made of a single layer that provides both acquisition and distribution functionality.

Hence, an ADS provided between the topsheet and the absorbent core can help reduce leakage of body liquids in the form of free-flowing liquid on the topsheet that may leak out of the absorbent article and that may also negatively affect skin health.

However, there is also a risk that liquid cannot be absorbed into the absorbent core quickly enough and thus flows through the absorbent core onto the backsheet. Especially in situations where a high gush volume is disposed into the absorbent article in only a few seconds, the ADS between the absorbent core and the topsheet may not have sufficient void volume to temporarily hold the liquid before it can be absorbed into and stored in the absorbent material of the absorbent core. Especially when the absorbent core has a relatively high percentage of superabsorbent polymer material, absorption of liquid into the superabsorbent polymer material may not be fast enough to handle a larger amount of liquid in a sufficient manner (as superabsorbent polymer materials typically absorb liquid slower than a layer of pure airfelt, especially when the superabsorbent polymer material has not been previously wetted, i.e. when a first gush of liquid is disposed into the article).

Even though the backsheet is generally liquid impervious, moisture or vapor of liquid that pools between the absorbent core and the backsheet may nevertheless penetrate the backsheet, leading to a cold, damp and unpleasant feel when the backsheet is touched from the outside (e.g. by a caregiver). This effect is further increased when a breathable backsheet is used. Such damp feel may not only be unpleasant, it may also lead to a premature diaper change long before the absorbent capacity of the absorbent article has been used up.

Another concern arises for the liquid that is not stored in superabsorbent polymer material but in the airfelt between the superabsorbent polymer (for absorbent core that are made of a mixture of airfelt and superabsorbent polymer material). This liquid also tends to be present rather in the areas of the absorbent core that is closer to the backsheet. Vapor of such liquid may also penetrate the backsheet, resulting in similar effects of a cold and damp touch as outlined in the foregoing paragraph.

Moreover, in addition to a damp and cold feel that may arise when vapor penetrates the backsheet, the presence of liquid within the absorbent article that is close to the backsheet also generates an unpleasant feeling when touching the absorbent article from the outside. This is not (only) due to the evaporation or movement through the film, but because heat conductivity of liquid is generally much higher than heat conductivity of air or of a relatively dry, lofty structure having air present in interstices and voids. For example, liquid provided newly into the absorbent article may initially give a warm feel from the outside whereas after some time this changes to a rather cold feel when touched from the outside.

Finally, liquid, such as urine, that stays closer to the backsheet leads to increased visibility of stains from the outside through the backsheet.

There is thus a need for absorbent articles that address the above problems. Hence, it is an objective of the present invention to provide an absorbent article that reduces or eliminates a cold and damp garment-facing surface of the backsheet—and at the same time can provide a dry wearer-facing surface.

SUMMARY OF THE INVENTION

Absorbent articles are typically configured with a focus of "locking fluid away" from the skin of the wearer. It has been found that, as a result, liquid is often distributed in the absorbent articles such that the majority of liquid is stored towards and close to the backsheet. Moreover, acquisition and distribution systems (ADS) are typically provided only in between the topsheet and the absorbent core, contributing to fast transport of liquid away from the skin of the wearer and maintenance of a dry absorbent article surface facing the wearer (i.e. the topsheet). Consequently, as set out above, vapor and moisture can penetrate the (liquid impermeable but often breathable) backsheet. To address these drawbacks, the inventors have found that liquid should not only be transported and locked away from the skin of the wearer, but the liquid should be stored deep inside the absorbent article, i.e. away from both the wearer- and garment-facing surface.

As a result, an absorbent article is provided which has a lower ADS. The lower ADS serves as an additional layer between the layer of absorbent material and the backsheet. That way, liquid, that is adjacent to the surface of the layer of absorbent material that faces towards the backsheet, is no longer in direct contact with the backsheet. Moreover, liquid that would otherwise penetrate through the backsheet, e.g. in gush situations where larger amounts of liquid are disposed into the absorbent article in a very short time, can be acquired and temporarily held by the lower ADS, to be subsequently absorbed back into the layer of absorbent material for ultimate storage.

The inventors have tested a large number of currently marketed absorbent articles to determine how the liquid is distributed within the absorbent article in the thickness direction, i.e. how much liquid is stored closer to the topsheet and how much liquid is stored closer to the backsheet. To this end, NMR technology has been employed and a test method has been established that enables the provision of precise liquid distribution profiles. This method was chosen because of its non-destructive nature and because it reflects well the actual in-use conditions of absorbent articles. The general NMR test method and apparatus are described in U.S. Pat. Nos. 10,371,652 and 10,365,237. Based on the general principles of the NMR test procedure, an optimized distribution profile has been developed which is obtained by the use of an appropriate lower ADS that reduces the amount of liquid towards the backsheet below a threshold of less than 80 µl, i.e. 0.08 ml (adding up the amount of liquid measured in three different locations and following the test protocol set out herein). Similarly, the amount of liquid towards the topsheet is very low, i.e. below 90 µl. All these amounts of liquid correspond to a measurement area of 1.9 cm by 1.9 cm and a measurement depth of 800 µm (i.e. 0.0008 m).

The present invention relates to an absorbent article comprising:
  a topsheet, a backsheet, and a layer of absorbent material interposed between the topsheet and backsheet, wherein the layer of absorbent material comprises superabsorbent polymer, and
  a lower acquisition and distribution system with at least one woven layer or, preferably, at least one nonwoven layer, the lower acquisition and distribution system being interposed between the layer of absorbent material and the backsheet; and
  optionally an upper acquisition and distribution system with at least one layer, the upper acquisition and distribution system being interposed between the layer of absorbent material and the topsheet.

The layer of absorbent material may consist of a single layer or may comprise two or more sub-layers. The sub-layers may be the same or may differ from each other, e.g. in size, composition, thickness etc., or in combinations thereof.

The absorbent article has a first zone corresponding to 800 µm (i.e. 0.0008 m) starting from and including the topsheet and extending towards the backsheet, and a second zone corresponding to 800 µm starting from and including the backsheet and extending towards the topsheet.

The absorbent article has a total amount of liquid of less than 90 µl, or less than 80 µl, or less than 75 µl in the first zone and a total amount of liquid of less than 80 µl, or less than 75 µl, in the second zone, upon being subjected to the NMR MOUSE method set out herein, determining and adding up the amount of liquid in three defined locations.

For the total amount of liquid in the first or second zone, the amount of liquid is measured in three defined locations, namely at the loading point (i.e. where the liquid has been introduced into the absorbent article for the NMR test), 4 cm away from the loading point towards the back waist region at the longitudinal centerline, and 8 cm away from the loading point towards the back waist region at the longitudinal centerline. The measured amounts at these three locations is added up and the sum is reported as "total amount of liquid" in the first or second zone.

Moreover, the amount of liquid at the loading point in the first zone as measured by the NMR MOUSE test method set out herein, may not be more than 50 µl, or may not be more than 40 µl, or may not be more than 35 µl. The amount of liquid at the loading point in the second zone as measured by the NMR MOUSE test method set out herein, may not be more than 50 µl, or may not be more than 40 µl, or may not be more than 35 µl.

Hence, in the absorbent article of the present invention, the liquid is held inside the absorbent article, leaving the regions adjacent to the inner, wearer-facing as well as the outer, garment-facing surface of the absorbent article with only minor amounts of liquid.

Liquid distribution within the absorbent article is measured by using NMR MOUSE (Nuclear Magnetic Resonance Mobile Universal Surface Explorer) methodology. NMR MOUSE is a portable device using an open NMR sensor to characterize fluid positioning inside a porous media structure (i.e. the absorbent article). The method enables precise determination of liquid distribution.

For the present invention, the NMR MOUSE technology is used to determine the amount of liquid within the first and second zone. For this, two gushes of liquid are introduced into the absorbent article, following the detailed test protocol set out below. For smaller absorbent articles, smaller amounts of liquid are used in the test method compared to larger absorbent articles (due to the overall lower liquid capacity of smaller absorbent articles, see details below), to better reflect in-use conditions of absorbent articles of different sizes. The amount of liquid in the first and second zone is measured by NMR MOUSE. The amount is measured at the loading point (i.e. the area where the liquid has been introduced into the absorbent article), 4 cm away from the loading point towards the rear waist region at the longitudinal centerline of the absorbent article and 8 cm away from the loading point towards the rear waist region at the longitudinal centerline of the article. The amount of liquid in these three locations is totaled. The sum is the total amount of liquid that is reported by the test method, whereas the amount of liquid at the loading point, i.e. excluding the amount of liquid 4 cm and 8 cm away from the loading point, is reported as "amount of liquid at the loading point".

According to the present invention, in the first zone, less than 90 µl, or less than 80 µl, or less than 75 µl of liquid is present in total in the three locations (combined) as determined by the NMR MOUSE test method set out herein. Also, in the second zone, less than 80 µl, or less than 75 µl of liquid is present in total in the three locations (combined) as determined by the NMR MOUSE test method set out herein. To illustrate the order of magnitude reflected by the liquid amount of less than 90 μl, and 80 μl, respectively: The protocol of the test method requires that a total of 150 ml is introduced into the absorbent article of larger sizes in the two subsequent gushes of equal amount and a total of 80 ml is introduced into smaller absorbent articles in two subsequent gushes of equal amount.

The basis weight of the lower acquisition and distribution system may be from 20 g/m² to 80 g/m².

The lower acquisition and distribution system may have a dry opacity of at least 25%.

The layer of absorbent material may extend longitudinally and transversely beyond the upper and lower acquisition and distribution system.

BRIEF DESCRIPTION OF THE DRAWINGS

While the specification concludes with claims particularly pointing out and distinctly claiming the present invention, it is believed that the same will be better understood from the following description read in conjunction with the accompanying drawings in which:

FIG. 2B is a transversal cross-section of the diaper of FIG. 1, showing a lower acquisition and distribution system between and in direct contact with the layer of absorbent material and a lower substrate layer.

FIG. 2C is a transversal cross-section of still another alternative diaper showing the lower acquisition and distribution layer between and in direct contact with the layer of absorbent material and the backsheet.

FIG. 12A illustrates a top plate assembly used in the Modified Fluid Acquisition Test.

FIG. 12B illustrates equipment used in the Modified Fluid Acquisition Test.

DETAILED DESCRIPTION OF THE INVENTION

Definition of Terms

Figure 1:
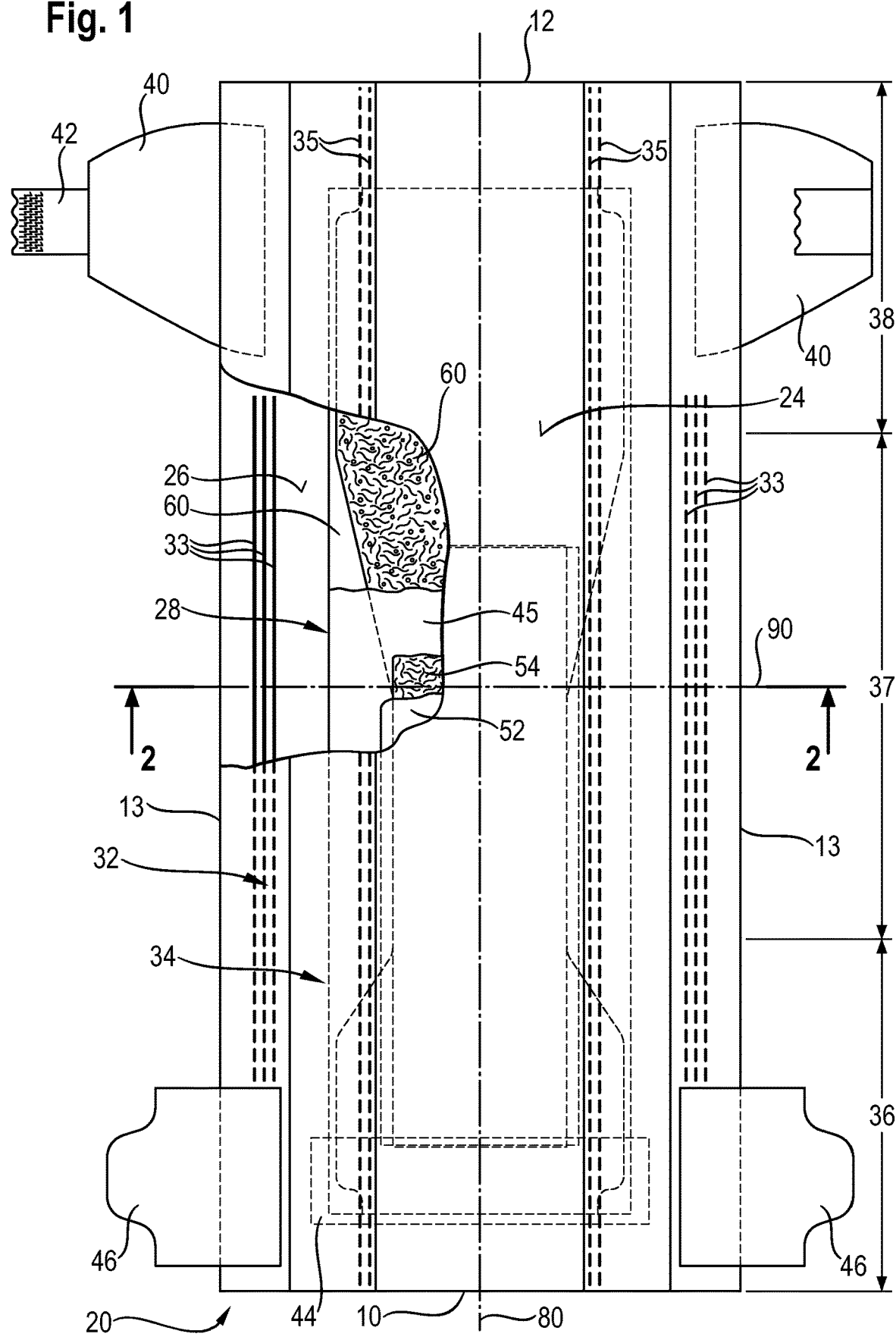
FIG. 1 is an exemplary absorbent article in the form of a diaper.

As used herein, "absorbent article" refers to devices that absorb and contain body exudates, and, more specifically, refers to devices that are placed against or in proximity to the body of the wearer to absorb and contain the various exudates discharged from the body. Absorbent articles include diapers (baby and infant diapers as well as diapers for adult incontinence), pants (for babies, infants and for adults), absorbent inserts (which are intended to be inserted into an outer cover to form a diaper or pant), feminine care absorbent articles such as sanitary napkins and pantiliners, and the like. As used herein, the term "exudates" includes, but is not limited to, urine, blood, vaginal discharges, sweat and fecal matter. Preferred absorbent articles of the present invention are disposable absorbent articles, more preferably disposable diapers and disposable pants.

As used herein, "diaper" and "pant" refers to an absorbent article generally worn by babies, infants and incontinent adults about the lower torso so as to encircle the waist and legs of the wearer and that is specifically adapted to receive and contain urinary and fecal waste. In a pant, as used herein, the longitudinal edges of the first and second waist region are attached to each other to a pre-formed waist opening and leg openings. A pant is placed in position on the wearer by inserting the wearer's legs into the leg openings and sliding the pant absorbent article into position about the wearer's lower torso. A pant may be pre-formed by any suitable technique including, but not limited to, joining together portions of the absorbent article using re-fastenable and/or non-refastenable bonds (e.g., seam, weld, adhesive, cohesive bond, fastener, etc.). A pant may be pre-formed anywhere along the circumference of the article (e.g., side fastened, front waist fastened). In a diaper, the waist opening, and leg openings are only formed when the diaper is applied onto a wearer by (releasable) attaching the longitudinal edges of the first and second waist region to each other on both sides by a suitable fastening system.

As used herein, a "pantiliner" and a "sanitary napkin" generally have two end regions and a middle region (i.e. a crotch region). The pantiliner and the sanitary napkin have a body-facing surface and a garment facing surface. The size and shape of the absorbent structure positioned between the topsheet and the backsheet can be altered to meet absorbent capacity requirements, and to provide comfort to the wearer. The garment facing surface of the pantiliner and of the sanitary napkin can have thereon pressure sensitive adhesive for affixing to a wearer's undergarments. Typically, such adhesive is covered with a release strip which is removed before affixing to the undergarment. Pantiliners can also be provided with lateral extensions known commonly in the art as "flaps" or "wings" intended to extend over and cover the panty elastics in the crotch region of the user's undergarment. However, wings are normally not used with pantiliners but are more often used in sanitary napkins. Sanitary napkins and pantiliners of the present invention comprise barrier leg cuffs.

As used herein, "disposable" is used in its ordinary sense to mean an article that is disposed or discarded after a limited number of usages over varying lengths of time, for example, less than 20 usages, less than 10 usages, less than five usages, or less than two usages. If the disposable absorbent article is a diaper, a pant, sanitary napkin, sanitary pad or wet wipe for personal hygiene use, the disposable absorbent article is most often intended to be disposed after single use.

The term "layer of absorbent material" as used herein refers to a component, which is placed or is intended to be placed within an absorbent article between the topsheet and the backsheet. The layer of absorbent material may be enclosed by a core wrap. The core wrap may be formed of an upper substrate layer, such as a nonwoven web, and a lower substrate layer, such as a nonwoven web. The lower substrate layer may be formed of the lower ADS, or by a layer of the lower ADS. The layer of absorbent material may be cellulose fibers (so-called "airfelt" or "fluff pulp"), synthetic absorbent fibers, superabsorbent material, or combinations thereof. The layer of absorbent material may be a mixture of cellulose fibers and superabsorbent material. The layer of absorbent material may also comprise minor amounts of adhesive (e.g. less than 2.0 weight-%, or less than 1.5 weight-%, or less than 1.0 weight-% of adhesive based on the total weight of the layer of absorbent material). The layer of absorbent material of the present invention comprises superabsorbent material, the layer of absorbent material may comprise at least 30 weight-%, or at least 40 weight-%, or at least 50 weight-%, or at least 60 weight-%, or at least 70 weight-%, or at least 80 weight-% or at least 90 weight-% by total weight of the layer of absorbent material. The superabsorbent material may be in the form of superabsorbent polymer fibers, superabsorbent polymer foams, or, preferably, superabsorbent polymer particles.

As used herein, the terms "nonwoven web" and "nonwoven layer" are used interchangeably. They refer to a material which is a manufactured web/layer of directionally or randomly oriented fibers. The fibers may be of natural or man-made origin. Natural fibers may be selected from the group consisting of wheat straw fibers, rice straw fibers, flax fibers, bamboo fibers, cotton fibers, jute fibers, hemp fibers, sisal fibers, bagasse fibers, Hesper aloe fibers, miscanthus, marine or fresh water algae/seaweeds, silk fibers, and combinations thereof. Preferably, the natural fibers are selected from the group consisting of cotton fibers, bamboo fibers, or mixtures thereof. Preferably, the natural fibers are cotton fibers. Synthetic fibers may be selected from the group consisting of polyolefins (such as polyethylene, polypropylene or combinations and mixtures thereof), polyethylene terephthalate (PET), co PET, polylactic acid (PLA), polyhydroxy alkanoid (PHA), or mixtures or combinations thereof.

The fibers in a nonwoven web are consolidated by friction, and/or cohesion and/or adhesion, excluding paper and products which are woven, knitted, tufted, stitch-bonded. The fibers may be staple fibers (e.g. in carded nonwoven webs/layers) or continuous fibers (e.g. in spunbonded or meltblown nonwoven webs/layers).

Nonwoven webs/layers can be formed by many processes such as meltblowing, spunlaying, solvent spinning, electro-spinning, and carding, and the fibers can be consolidated, e.g. by hydroentanglement (in spunlaced nonwoven webs/layers), air-through bonding (using hot air that is blown through the fiber layer in the thickness direction), needle-punching, one or more patterns of bonds and bond impressions created through localized compression and/or application of heat or ultrasonic energy, or a combination thereof. The fibers may, alternatively or in addition, be consolidated by use of a binder. The binder may be provided in the form of binder fibers (which are subsequently molten) or may be provided in liquid, such as a styrene butadiene binder. A liquid binder is provided to the fibers (e.g. by spraying, printing or foam application) and is subsequently cured to solidify.

The basis weight of nonwoven fabrics is usually expressed in grams per square meter ($g/m^2$).

"Monocomponent" refers to fiber formed of a single polymer component or single blend of polymer components, as distinguished from bicomponent or multicomponent fiber.

"Bicomponent" refers to fibers having a cross-section comprising two discrete polymer components, two discrete blends of polymer components, or one discrete polymer component and one discrete blend of polymer components. "Bicomponent fiber" is encompassed within the term "multicomponent fiber." A bicomponent fiber may have an overall cross section divided into two subsections of the differing components of any shape or arrangement, including, for example, concentric core-and-sheath subsections, eccentric core-and-sheath subsections, side-by-side subsections, radial subsections, etc.

"Multicomponent fiber" includes, but is not limited to, "bicomponent fiber." A multicomponent fiber may have an overall cross section divided into subsections of the differing components of any shape or arrangement, including, for example, coaxial subsections, concentric core-and-sheath subsections, eccentric core-and-sheath subsections, side-by-side subsections, islands-in the sea subsection, segmented pie subsections, etc.

The term "dtex" as used herein refers to a unit used to indicate the fineness of a filament/fiber. The unit expresses the mass of a filament/fiber in grams per 10,000 meters of length.

The term "mechanically deformed" and "mechanical deformation" as used herein means that one or more nonwoven webs are mechanically deformed between a first and second roll. If more two or more nonwoven webs are laid on top of each other prior to mechanically deforming them, the webs are intimately combined at the same time as they are mechanically deformed. The mechanical deformation depends on the process, the required apparatus but also on the properties of the substrate, i.e. apparent elongation of the fibers, fiber mobility, ability to deform and stretch in the area where the mechanical deformation is formed, ability to undergo plastic deformation which sets after existing the first and second roll, or springing partially back due to elastic recovery.

The mechanical deformation may comprise engaging a single nonwoven web or more than one nonwoven web between a first and second forming member such that a plurality of deformations comprising three-dimensional protrusions are obtained. Mechanical defamation may also introduce apertures in the nonwoven, such that a three-dimensional, apertured nonwoven web is obtained. Known processes to mechanically deform a nonwoven web are "selfing" and "ring-rolling". They are described e.g. in WO2016/040090A1.

As used herein, mechanical deformation does not include embossing of a nonwoven web (though the nonwoven web may be embossed in addition to being mechanical deformed).

"Hydrophilic" describes surfaces of substrates which are wettable by aqueous fluids (e.g., aqueous body fluids) deposited on these substrates. Hydrophilicity and wettability are typically defined in terms of contact angle and the strike-through time of the fluids, for example through a nonwoven fabric. This is discussed in detail in the American Chemical Society publication entitled "Contact Angle, Wettability and Adhesion", edited by Robert F. Gould (Copyright 1964). A surface of a substrate is said to be wetted by a fluid (i.e., hydrophilic) when either the contact angle between the fluid and the surface is less than 90°, or when the fluid tends to spread spontaneously across the surface of the substrate, both conditions are normally co-existing. Conversely, a substrate is considered to be "hydrophobic" if the contact angle is greater than 90° and the fluid does not spread spontaneously across the surface of the fiber.

"Longitudinal" refers to a direction running substantially perpendicular from a waist edge to an opposing waist edge of the article and generally parallel to the maximum linear dimension of the article. "Transverse" refers to a direction perpendicular to the longitudinal direction.

"Inner" and "outer" refer respectively to the relative location of an element or a surface of an element or group of elements. "Inner" implies the element or surface is nearer to the body of the wearer during wear than some other element or surface. "Outer" implies the element or surface is more remote from the body of the wearer during wear than some other element or surface (i.e., element or surface is more proximate to the wearer's garments that may be worn over the present article).

"Body-facing" and "garment-facing" refer respectively to the relative location of an element or a surface of an element or group of elements. "Body-facing" implies the element or surface is nearer to the wearer during wear than another element of the same component. An example is the inner layer of the elastic laminate of the present invention wherein the inner layer (being an element of the elastic laminate) is nearer to the body of the wearer than the outer layer (being another element of the elastic laminate). "Garment-facing" implies the element or surface is more remote from the wearer during wear than another element of the same component. The garment-facing surface may face another (i.e. other than the wearable article) garment of the wearer, other items, such as the bedding, or the atmosphere.

FIG. 1 is a plan view of an exemplary diaper 20, in a flat-out state, with portions of the diaper being cut-away to more clearly show the construction of the diaper 20. As said, this diaper 20 is shown for illustration purpose only as the structure of the present invention may be comprised in a wide variety of diapers or other absorbent articles, such as pants.

As shown in FIG. 1, the absorbent article, here a diaper, comprises a topsheet 24, backsheet 26, and a layer of absorbent material 28 which is positioned between the topsheet 24 and the backsheet 26. The layer of absorbent material 28 can absorb and contain liquid received by the absorbent article. The absorbent article of the present invention, such as the diaper 20 illustrated in FIG. 1, comprises a lower acquisition and distribution system and may also comprise an upper acquisition and distribution system (ADS) 50. The upper ADS may comprise an upper 52 and lower 54 layer.

The absorbent article may also comprise barrier leg cuffs 34 and may further comprise elasticized leg cuffs 32. Moreover, the absorbent article may comprise a fastening system, such as an adhesive fastening system or a hook and loop fastening member, which can comprise tape tabs 42, such as adhesive tape tabs or tape tabs comprising hook elements, cooperating with a landing zone 44 (e.g. a nonwoven web providing loops in a hook and loop fastening system).

The diaper or pant, such as the diaper 20 shown in FIG. 1 can be notionally divided in a first waist region 36 (which may be the front waist region), a second waist region 38 (which may be the back waist region) opposed to the first waist region 36 and a crotch region 37 located between the first waist region 36 and the second waist region 38. The longitudinal centerline 80 is the imaginary line separating the diaper along its length in two equal halves. The transversal centerline 90 is the imagery line perpendicular to the longitudinal line 80 in the plane of the flattened-out diaper and going through the middle of the length of the diaper (the same applies to for the transversal centerline and longitudinal line of other absorbent articles of the present invention). The periphery of the diaper 20 is defined by the outer edges of the diaper 20. The longitudinal edges 13 of the diaper may run generally parallel to the longitudinal centerline 80 of the diaper 20 and the end edges (the front waist edge 10 and the back waist edge 12) run between the longitudinal edges generally parallel to the transversal centerline 90 of the diaper 20. The crotch region, the first and the second waist region each constitute ⅓ of the absorbent article along the longitudinal centerline.

Further, the absorbent article may comprise other elements, such as a back waist feature, which may be non-elastic or elastic, and a front waist feature, which may be non-elastic or elastic, a lotion applied onto the body-facing surface of the topsheet, back ears 40, and/or front ears 46.

The front and/or back ears 40, 46 may be separate components attached to the absorbent article or may instead be continuous with portions of the topsheet and/or backsheet such that these portions form all or a part of the front and/or back ears 40, 46. Also combinations of the aforementioned are possible, such that the front and/or back ears 40, 46 are formed by portions of the topsheet and/or backsheet while additional materials are attached to form the overall front and/or back ears 40, 46. The front and/or back ears may be elastic or non-elastic. Also, the front ears 40 may be applied as separate components attached to the absorbent article while the back ears (or parts thereof) 46 may be continuous with portions of the backsheet and/or topsheet—or vice versa.

The topsheet 24, the backsheet 26, and the layer of absorbent material 28 may be assembled in a variety of well-known configurations, in particular by gluing, heat embossing, ultrasonic bonding or combinations thereof. Exemplary diaper configurations are described generally in U.S. Pat. Nos. 3,860,003; 5,221,274; 5,554,145; 5,569,234; 5,580,411; and 6,004,306.

The topsheet 24 is the part of the absorbent article 10 that is in contact with the wearer's skin. The topsheet 24 may be joined to portions of the backsheet 26, the layer of absorbent material 28, to an upper nonwoven core web overlaying the layer of absorbent material towards the topsheet, to the barrier leg cuffs 32, and/or to any other layers as is known to those of ordinary skill in the art. The topsheet 24 may be compliant, soft-feeling, and non-irritating to the wearer's skin. Further, at least a portion of, or all of, the topsheet may be liquid permeable, permitting liquid bodily exudates to readily penetrate through its thickness. A suitable topsheet may be manufactured from a wide range of materials, such as porous foams, reticulated foams, apertured plastic films, woven materials, nonwoven materials, woven or nonwoven materials of natural fibers (e.g., wood or cotton fibers), synthetic fibers or filaments (e.g., polypropylene or bicomponent PE/PP fibers or mixtures thereof), or a combination of natural and synthetic fibers. The topsheet may have one or more layers. The topsheet may be apertured or non-apertured, and may have any suitable three-dimensional features, and/or may have a plurality of embossments (e.g., a bond pattern). Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet.

The backsheet 26 is generally that portion of the absorbent article 20 that constitutes all or a part of the garment-facing surface of the absorbent article. The backsheet 26 may be joined to portions of the topsheet 24, the layer of absorbent material 28, a to a lower nonwoven core web, to the lower acquisition and distribution system (or to the layer of the lower ADS that is in direct contact with the backsheet and/or any other layers of the absorbent article by any attachment methods known to those of skill in the art. The backsheet 26 prevents, or at least inhibits, the bodily exudates absorbed and contained in the layer of absorbent material 28 from soiling articles such as bedsheets, undergarments, and/or clothing. The backsheet is typically liquid impermeable, or at least substantially liquid impermeable.

The backsheet may, for example, be or comprise a thin plastic film 39, such as a thermoplastic film having a thickness of about 0.012 mm to about 0.051 mm Other suitable backsheet materials may include breathable materials which permit vapors to escape from the absorbent article, while still preventing, or at least inhibiting, bodily exudates from passing through the backsheet.

The backsheet may be breathable. A breathable backsheet may have a Water Vapor Transmission Rate (WVTR) of from 1,000 to 15,000 g/m$^2$/h, or from 1,000 to 10,000 g/m$^2$/h, or from 1,500 to 10,000 g/m$^2$/h as measured using a PERMATRAN-W Model 101K (available from Mocon, Inc., Minneapolis, MN) or equivalent, according to Nonwovens Standard Procedure NWSP 70.4.R0(15) with the following specifications: experiments were carried out in a lab controlled at 23° C.±2 C.° and 50% RH±2% RH and the instrument cells heated to 37.8° C. (100° F.).

The backsheet 26 may comprise a backsheet outer cover nonwoven web 40. The backsheet outer cover nonwoven web may comprise one or more nonwoven materials joined to a backsheet film 39 and that covers the backsheet film 39. The outer cover nonwoven web 40 may form the garment-facing surface of the backsheet. Thereby, film may not be present on the garment-facing surface. The backsheet outer cover nonwoven web 40 may comprise a bond pattern, apertures, and/or three-dimensional features.

The absorbent article 20 may have a length of more than 450 mm, or less than 450 mm. The length of the absorbent article is determined when the absorbent article is laid flat, with all elastics strands hindering a flattened out configuration (such as leg elastics) being cut and thus de-elasticized). The length is determined along the longitudinal centerline.

The layer of absorbent material 28 comprises superabsorbent polymer particles, and optionally cellulose fibers. The layer of absorbent material may be supported by one or more substrate layers. An upper substrate layer 45 may be provided between the upper ADS 50 and the layer of absorbent material 28. If the absorbent article does not comprise an upper ADS, the upper substrate layer may be provided between the topsheet and the layer of absorbent material. A lower substrate layer 46 may be provided between the layer of absorbent material 28 and the lower ADS. Alternatively to the lower substrate layer 46, the lower ADS 60 may be in direct contact with the layer of absorbent material 28 (i.e. there is no lower substrate layer 46).

The upper substrate layer 45 and the lower substrate layer 46 may partly or fully enclose the layer of absorbent material 28. Alternatively, the upper substrate layer 45 and the lower ADS 60 may partly or fully enclose the layer of absorbent material 28.

Figure 2A:
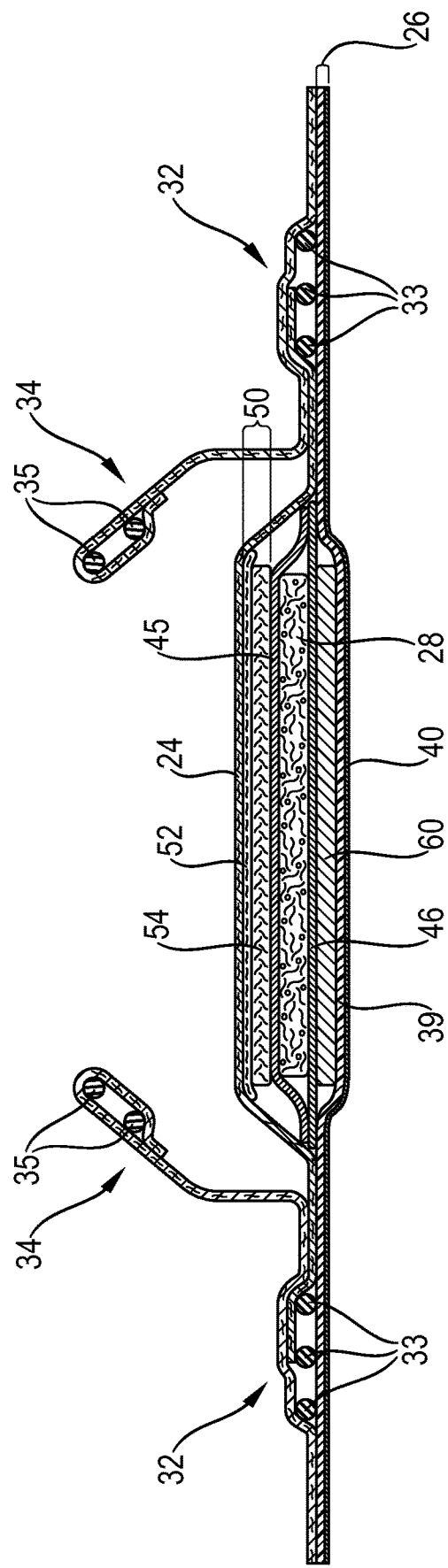
FIG. 2A is a transversal cross-section of the diaper of FIG. 1 showing a lower acquisition and distribution layer between and in direct contact with a lower substrate layer and the backsheet.

The layer of absorbent material 28 may be partly or fully enclosed by and in direct contact with an upper and a lower substrate layer 45, 46, the upper substrate layer 45 may be between the layer of absorbent material 28 and the upper acquisition and distribution system 50, and the lower substrate layer 46 may be between the layer of absorbent material 28 and the lower acquisition and distribution system 60. Such an embodiment is exemplarily shown in FIG. 2A. In such embodiments, a) the lower acquisition and distribution system 60 may be hydrophobic and the lower substrate layer 46 may be hydrophilic; or b) the lower acquisition and distribution system 60 and the lower substrate layer 46 may both be hydrophilic and the lower acquisition and distribution system 60 may be less hydrophilic than the lower substrate layer 46; or c) the lower acquisition and distribution system 60 and the lower substrate layer 46 may both be hydrophobic and the lower substrate layer 46 may be less hydrophobic than the lower acquisition and distribution system 60.

Alternatively, the layer of absorbent material 28 and the lower acquisition and distribution system 60 may be partly or fully enclosed by and in direct contact with an upper and a lower substrate layer 45, 46, and the upper substrate layer 45 may be between the layer of absorbent material 28 and the upper acquisition and distribution system 50, and the lower substrate layer 46 may be between the lower acquisition and distribution system 60 and the backsheet, with the layer of absorbent material 28 being in direct contact with the lower acquisition and distribution system 60. An embodiment of such configuration is exemplified in FIG. 2C.

In still another alternative, the layer of absorbent material 28 may be partly or fully enclosed by and in direct contact with an upper substrate layer 45 and the lower acquisition and distribution system 60, and the upper substrate layer 45 may be between the layer of absorbent material 28 and the upper acquisition and distribution system 50. Such an embodiment is exemplarily illustrated in FIG. 2B.

The upper and the lower substrate layer may be made of the same material, i.e. of the same nonwoven web, or they may be made of different materials, i.e. two nonwoven webs which are different from each other. The upper and lower substrate layer may also be made of a single, continuous material, such as a single, continuous nonwoven web, which is wrapped around the layer of absorbent material, e.g. in a c-wrap configuration.

Portions at and adjacent to the longitudinal edges of the upper substrate layer 45 may be folded over the longitudinal edges of the layer of absorbent material, such that these portions are positioned on the garment-facing surface of the layer of absorbent material. Alternatively or in addition, portions at and adjacent to the longitudinal edges of the lower substrate layer 46 may be folded over the longitudinal edges of the layer of absorbent material, such that these portions are positioned on the body-facing surface of the layer of absorbent material The layer of absorbent material may be immobilized on the upper substrate layer 45 and/or on the lower substrate layer 46, and/or on the lower ADS 60, for example by use of hot melt adhesive.

The upper and lower substrate layer 45, 46 may be any material capable of supporting the layer of absorbent material. It may be a web or sheet material, such as foam, film, woven or, preferably, a nonwoven web. The upper and lower substrate layer 45, 46 may be distinct separate sheets of material (such as two nonwoven webs) or may be formed of a continuous sheet (such as a continuous nonwoven web) which is wrapped around the layer of absorbent material.

The layer of absorbent material 28 comprises superabsorbent polymer, such as superabsorbent polymer particles, and may optionally comprise cellulose fibers.

The layer absorbent material may include comprise at least 30 weight-%, or at least 40 weight-%, or at least 50 weight-%, or at least 60 weight-%, or at least 70 weight-%, or at least 80 weight-% or at least 90 weight-% of superabsorbent polymer, such as superabsorbent polymer particles, by total weight of the absorbent layer. The layer of absorbent material may comprise less than 25 weight-%, or less than 20weight-%, or less than 15 weight-%, or less than 10 weight-% of cellulose, or less than 5% by weight of cellulose, or even no cellulose based on the total weight of the layer of absorbent material.

The superabsorbent polymer particles and the cellulose fibers may be homogeneously mixed with each other such that the ratio of cellulose fibers to superabsorbent polymer particles is substantially the same throughout the layer of absorbent material. Alternatively, the superabsorbent polymer particles and the cellulose fibers may be non-homogeneously mixed such that the ratio of cellulose fibers to superabsorbent polymer particles is higher towards the front and rear edges of the layer of absorbent material compared to a central area of the layer of absorbent material. The area towards the front edge of the layer of absorbent material, the area towards the rear edge of the layer of absorbent material, and the central area may each extend along ⅓ of longitudinal dimension of the layer of absorbent material along the longitudinal centerline.

When the layer of absorbent material is cellulose free, the only absorbent material in the absorbent layer may be superabsorbent polymer (particles, fibers or foam). The resulting layer of absorbent material has a reduced thickness in the dry state compared to conventional absorbent cores including cellulosic fibers. The reduced thickness helps to improve the fit and comfort of the absorbent article for the wearer.

The layer of absorbent material may comprise one or more areas where no absorbent material is present and which are completely surrounded by absorbent material. Hence, these areas may free of cellulose fibers and superabsorbent polymer particles. The areas being free of absorbent material may be elongated areas having a length of from 20% and 80%, or from 20% to 70%, or from 30% to 60%, by total longitudinal dimension of the layer of absorbent material. The elongate areas may be straight, curved, or combinations thereof. The layer of absorbent material may only have one area free of absorbent material or may comprise two or more areas free of absorbent material. Two or more areas free absorbent material may be configured such that they are symmetric with respect to the longitudinal centerline of the absorbent article.

The superabsorbent polymer particles comprised by the layer of absorbent material may be spherical, spherical-like, ellipsoid, or irregularly shaped, such as ovoid-shaped particles of the kind that may be obtained from inverse phase suspension polymerizations. The particles may, optionally, be agglomerated at least to some extent to form larger irregular agglomerations of particles.

The superabsorbent polymer particles may be selected from among polyacrylates and polyacrylate based materials that are internally and/or surface cross-linked, such as for example partially neutralized cross-linked polyacrylates or acid polyacrylate. Examples of absorbent polymer particles suitable in the present disclosure are described for instance in the PCT Pat. App. Nos. WO 07/047598, WO 07/046052, WO2009/155265 and WO2009/155264.

Due to the presence of the lower ADS, the absorbent article of the present invention has fast acquisition speed, as is reflected by the total acquisition time of the various examples below. The total acquisition time of the absorbent article may be less than 120 seconds, or less than 100 seconds, as measured according to the test method set out herein.

Upper Acquisition and Distribution System (ADS)

An upper ADS 50 may be disposed between the layer of absorbent material 28 and the topsheet 24. The upper ADS may be in direct contact with the layer of absorbent material 28 and with the topsheet 24. If the absorbent article comprises an upper substrate layer that at least partially encloses the layer of absorbent material 28, the upper ADS may be in direct contact with the topsheet 24 and the upper substrate layer 45.

The upper ADS may serve as a temporary reservoir for liquid until the layer of absorbent material can absorb and store the liquid, and for subsequent distribution of the liquid into the layer of absorbent material in an efficient manner. The upper ADS may consist of a single layer or comprise multiple layers, such as an upper layer 52 provided adjacent to the topsheet 24 and facing towards the wearer's body, and a lower layer 54 provided between the upper layer 52 and the layer of absorbent material, facing towards garment of the wearer.

The prior art discloses many types of acquisition-distribution systems, see for example WO2000/59430, WO95/10996, U.S. Pat. No. 5,700,254, WO02/067809.

The upper ADS may be free of superabsorbent polymer. The upper ADS may also be free of unmodified cellulose fibers.

The function of a lower layer 54 of the upper ADS 50 is typically to spread the insulting fluid liquid over a larger surface within the absorbent article so that the absorbent capacity of the layer of absorbent material can be more efficiently used. The lower layer 54 of the upper ADS may be made of a nonwoven web based on synthetic or cellulosic fibers and having a relatively low density. The lower layer of the upper ADS may typically have an average basis weight of from 30 to 400 $g/m^2$, in particular from 80 to 300 $g/m^2$. The lower layer of the upper ADS may not be formed of a coherent, self-sustaining web or sheet but may be a layer with little integrity on its own.

The lower layer of the upper ADS may for example comprise at least 50%, or 60%, or 70%, or 80%, or 90% by weight of cross-linked cellulose fibers. The cross-linked cellulosic fibers may be crimped, twisted, or curled, or a combination thereof including crimped, twisted, and curled. The cross-linked cellulosic fibers provide higher resilience compared to non-modified cellulose fibers and therefore higher resistance against the compression in the product packaging or in use conditions of the absorbent article, e.g. under baby weight. This provides the lower layer of the upper ADS with a relatively high void volume, permeability and liquid absorption, and hence reduced leakage and improved dryness.

The lower layer of the upper ADS comprising cross-linked cellulose fibers, may comprise other fibers, but this layer may advantageously comprise at least 50%, or 60%, or 70%, or 80%, or 90% or even up to 100%, by weight of the layer, of cross-linked cellulose fibers. Examples of such mixed layer of cross-linked cellulose fibers may comprise 70% by weight of chemically cross-linked cellulose fibers, 10% by weight polyester (PET) fibers, and 20% by weight untreated pulp fibers. In another example, the layer of cross-linked cellulose fibers may comprise 70% by weight chemically cross-linked cellulose fibers, 20% by weight lyocell fibers, and 10% by weight PET fibers. In another example, the layer may comprise 68% by weight chemically cross-linked cellulose fibers, 16% by weight untreated pulp fibers, and 16% by weight PET fibers.

The upper ADS may further comprise an upper layer 52, whose function is typically to quickly acquire the fluid away from the topsheet so as to provide a good dryness for the wearer. The upper layer of the upper ADS is typically placed directly under the topsheet and directly above the lower layer of the upper ADS. The upper layer of the upper ADS may typically be or comprise a non-woven web, for example a SMS or SMMS material, comprising two outer spun-bonded (S) layers with one or more melt-blown (M) layers in between, or alternatively a carded nonwoven web comprising a binder to consolidate the fibers and provide web integrity. The nonwoven web may, in particular, be latex binder bonded. Exemplary upper layers for the upper ADS are disclosed in U.S. Pat. No. 7,786,341. Carded, resin-bonded nonwoven webs may be used, in particular where the fibers used are solid round or round and hollow PET staple fibers (such as a 50/50 or 40/60 mix of 6 denier and 9 denier fibers).

A carded resin-bonded upper layer of the upper ADS may be stabilized by a latex binder, for example a styrene-butadiene latex binder (SB latex). Processes for obtaining such lattices are known, for example, from EP 149 880 (Kwok) and US 2003/0105190 (Diehl et al.). The binder may be present in the upper layer of the upper ADS in excess of 15%, or of 20% by weight, but may be present by not more than 40%, or not more than 35% by weight of the upper layer. SB latex is, for example, available under the trade name GENFLO™ 3160 (OMNOVA Solutions Inc.; Akron, Ohio).

Lower Acquisition and Distribution System (ADS)

The lower ADS 60 is disposed between the layer of absorbent material 28 and the backsheet 26. The lower ADS may be in direct contact with the layer of absorbent material 28 and with the backsheet 26. If the absorbent article comprises a lower substrate layer 46 that, in conjunction with an upper substrate layer at least partially encloses the layer of absorbent material 28, the lower ADS may be in direct contact with the topsheet 24 and the lower substrate layer 45.

The lower ADS may serve as a temporary reservoir for liquid that has flown through the layer of absorbent material because it was not absorbed fast enough by the absorbent material of the layer of absorbent material.

Additional layers provided to an absorbent article generally increase the thickness and bulk of the article. This may lead to increased bending stiffness, and thus to drawbacks for conformity and close contact of the article to the wearer's body, thereby reducing wearer comfort. Also, increased bulk is generally not desirable, especially between the wearer's legs. Therefore, the thickness and bulk of the lower ADS should be carefully chosen.

To not unduly increase the stiffness of the absorbent article, the lower ADS may have a Horizontal Bending Drop according to the test method set out below, of greater than 60, preferably greater than 70. Higher values for the Horizontal Bending Drop indicate that a material is more flexible versus lower values.

On the other side, the lower ADS is preferably a relatively lofty material (such as spunlace or air-through bonded nonwoven webs), providing sufficient void volume to be able to acquire and hold fluid that penetrates through the layer of absorbent material. It has been found that, as the amount of fluid potentially penetrating through the layer of absorbent material is lower than the amount of liquid that generally needs to be handled by the upper ADS, the lower ADS may have a lower basis weight and lower thickness than the upper ADS. Also, the lower ADS may only consist of a single material, such as a single layer of material.

The basis weight of the lower ADS may be homogeneous throughout the length and width of the lower ADS (i.e. in the longitudinal and transverse direction). Such homogeneous basis weight should not take into account local basis weight variations on a rather small scale (such as variations within 1.0 cm, or within 0.5 cm in width and length direction), which may result from mechanical deformation of the lower ADS.

The lower ADS may have a smaller extension in the longitudinal and/or transverse direction than the layer of absorbent material, such that the layer of absorbent material extends beyond the lower ADS in longitudinal and/or transverse direction. The layer of absorbent material may also extend beyond the upper ADS in the longitudinal and/or transverse direction.

Alternatively, the lower ADS may have a larger extension in the longitudinal and/or transverse direction than the layer of absorbent material, such that the lower ADS extends beyond the layer of absorbent material in the longitudinal and/or transverse direction. This may be desirable when the layer of absorbent material is in direct contact with the lower ADS (i.e. when there is no lower substrate layer between the layer of absorbent material and the lower ADS). In such configurations, the layer of absorbent material may be partly or fully deposited and formed on the lower ADS. The layer of absorbent material may be partly formed on the lower ADS and partly on an upper substrate layer, and subsequently, both sub-components of the layer of absorbent material are combined to form the layer of absorbent material by putting the two sub-components in a face to face relationship.

The lower ADS may be free of superabsorbent polymer. The lower ADS may comprise or consist of a nonwoven web. It may be a spunbond or meltblown nonwoven web (made of continuous fibers) or a carded nonwoven web (made of staple fibers) or a nonwoven with spunbond and meltblown layers (e.g. an SMS, SMMS, SMSS or the like). The nonwoven web may be made of synthetic fibers, such as polyolefin (e.g. polyethylene, polypropylene or mixtures or combinations thereof), polyethylene terephthalate (PET), co-PET, polylactic acid (PLA), polyhydroxy alkanoid (PHA), or combinations or mixtures thereof. The fibers may be continuous or staple fibers.

The fibers may be monocomponent fibers or multicomponent fibers, such as bicomponent fibers. If the fibers comprised by the lower ADS are bicomponent fibers, they have a core-sheath configuration, wherein the core component has a higher melting point than the sheath component.

Preferably, the lower ADS comprises or consists of a nonwoven web which is air-through bonded or spunlace. Such nonwoven webs generally have high loft. Hence, they have a porous structure to provide void volume for absorbing and temporarily holding liquid. At the same time, they provide softness and do not have an excessively high bending stiffness (reflected by the Horizontal Bending Drop according to the test method set out below).

The fibers may be continuous, such as in a spunlaid nonwoven web. The spunlaid nonwoven web is preferably air-through bonded or spunlace. In addition to hydroentanglement (spunlace) or air-through bonding, the spunlaid nonwoven web may or may not have undergone some localized bonding with heat and/or pressure (e.g. point bonding), introducing localized bond regions where the fibers are fused to each other.

Preferably, however, the fibers comprised by the lower ADS are staple fibers. Similar to a nonwoven web made of continuous fibers, a nonwoven web of staple fibers is preferably air-through bonded or spunlace. In addition to hydroentanglement (spunlace) or air-through bonding, the nonwoven web of staple fibers may or may not have undergone some localized bonding with heat and/or pressure (e.g. point bonding), introducing localized bond regions where the fibers are fused to each other.

Irrespective whether the nonwoven web is made of continuous fibers or staple fibers, the localized bonding should however not bond an excessively large surface area, thus negatively impacting the loft and void volume of the nonwoven web. Preferably, the total bond area obtained by localized bonding with heat and/or pressure (in addition to hydroentanglement or air-through bonding) should not be more than 20%, or not be more than 15%, or not be more than 10% of the total surface area of the nonwoven web.

Alternatively, the nonwoven web comprised by the lower ADS should not have undergone any bonding and consolidation in addition to the hydroentanglement (spunlace) or air-through bonding. Thereby, the advantageous properties of such nonwoven webs can be used to their optimum.

In a spunlace nonwoven web the fibers have been subjected to hydroentanglement to intermingle and intertwine the fibers with each other. Cohesion and the interlacing of the fibers with one another may be obtained by means of a plurality of jets of water under pressure passing through a moving fleece or cloth and, like needles, causing the fibers to intermingle with one another. Thus, consolidation of a spunlace nonwoven web is essentially a result of hydraulic interlacing. "Spunlace nonwoven web", as used herein, also relates to a nonwoven formed of two or more precursor webs, which are combined with each other by hydraulic interlacing. The two or more webs, prior to being combined into one nonwoven by hydraulic interlacing, may have underdone bonding processes, such as heat and/or pressure bonding by using e.g. a patterned calendar roll and an anvil roll to impart a bonding pattern. However, the two or more webs are combined with each other solely by hydraulic interlacing. Alternatively, the spunlace nonwoven web is a single web, i.e. it is not formed of two or more precursor webs. Spunlace nonwoven layers/webs can be made of staple fibers or continuous fibers.

Through-air bonding (interchangeably used with the term "air-through bonding") means a process of bonding staple fibers or continuous fibers by forcing air through the nonwoven web, wherein the air is sufficiently hot to melt (or at least partly melt, or melt to a state where the fiber surface becomes sufficiently tacky) the polymer of a fiber or, if the fibers are multicomponent fibers, wherein the air is sufficiently hot to melt (or at least partly melt, or melt to a state where the fiber surface becomes sufficiently tacky) one of the polymers of which the fibers of the nonwoven web are made. The air velocity is typically between 30 and 90 meter per minute and the dwell time may be as long as 6 seconds. The melting and re-solidification of the polymer provide the bonding between different fibers.

Figure 13:
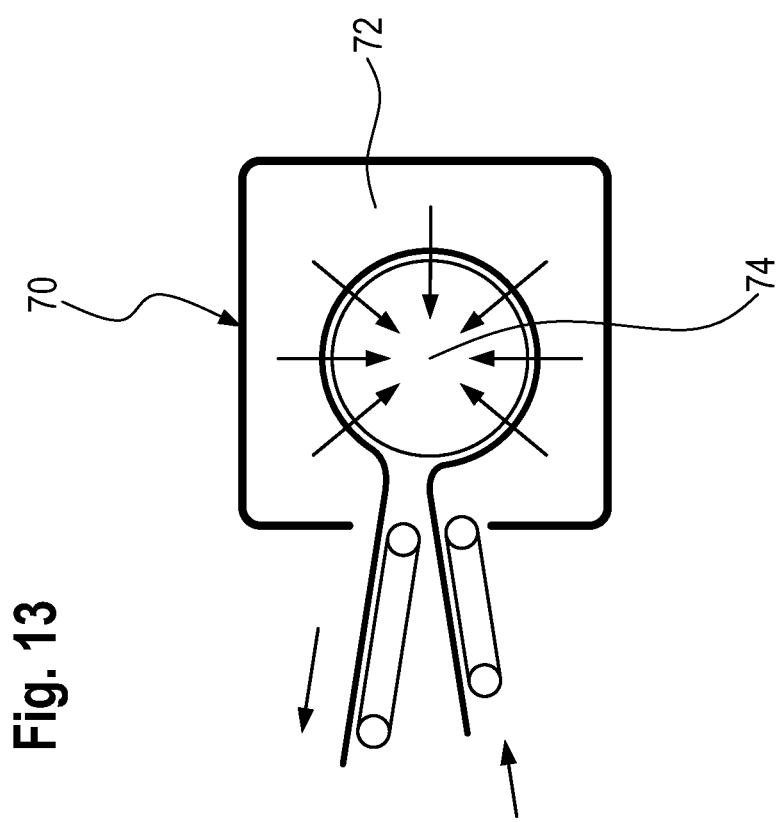
FIG. 13 is a schematic drawing of a through air bonder.

A through air bonder is schematically shown in FIG. 13. In the through-air bonder 70, air having a temperature above the melting temperature of the polymer of the staple fibers or continuous fibers or, if the staple or continuous fibers are multicomponent fibers, above the melting temperature of a first fiber component and below the melting temperature of a second fiber component, is directed from the hood 72, through the web, and into the perforated roller 74. Alternatively, the through-air bonder may be a flat arrangement wherein the air is directed vertically downward onto the web. The operating conditions of the two configurations are similar, the primary difference being the geometry of the web during bonding.

The hot air melts the staple or continuous fiber, or, for multicomponent fibers, the lower melting polymer component of the fiber and thereby forms bonds between the staple fibers to consolidate and integrate the layer of staple fibers into a web.

The nonwoven layer comprised by or forming the lower ADS may comprise multicomponent fibers. The fibers of the nonwoven comprised by the lower acquisition and distribution layer, may comprise at least 30 weight-%, or at least 40 weight-%, or at least 50 weight-%, or at least 70 weight-%, or at least 90 weight-% or 100 weight-% of multicomponent fibers based on the total weight of the nonwoven comprised by the lower acquisition and distribution layer. The multicomponent fibers may be bicomponent fibers, such as core-sheath or side-by-side bicomponent fibers.

Alternatively, the nonwoven layer comprised by or forming the lower ADS may comprise monocomponent fibers. The fibers of the nonwoven comprised by the lower acquisition and distribution layer, may comprise at least 30 weight-%, or at least 40 weight-%, or at least 50 weight-%, or at least 70 weight-%, or at least 90 weight-% or 100 weight-% of monocomponent fibers based on the total weight of the nonwoven comprised by the lower acquisition and distribution layer. The nonwoven web comprised by or forming the lower ADS may comprise a mixture of monocomponent fiber and multicomponent fibers.

As the nonwoven layer of the lower ADS is preferably a very lofty structure, the use of crimped fibers may be beneficial. Such fibers have also shown to provide the nonwoven layer with good resiliency, i.e. the nonwoven web has a relatively good ability to regain its original caliper (or most of its original caliper) after it has been compressed for a longer time (e.g. while being contained in a closed package that contains highly compressed absorbent articles). The crimped fibers may have flat crimp (so-called two-dimensional crimp) or three-dimensional crimp, such as spiral crimp. Bicomponent fibers are well known as being suitable for obtaining crimped fibers.

The fibers of the nonwoven comprised by the lower acquisition and distribution layer, may comprise at least 30 weight-%, or at least 40 weight-%, or at least 50 weight-%, or at least 70 weight-%, or at least 90 weight-% or 100 weight-% of crimped fibers based on the total weight of the nonwoven comprised by the lower acquisition and distribution layer. The crimped fibers may be bicomponent fibers.

The caliper of the lower acquisition and distribution system is desirably in a range that balances good liquid absorption and liquid holding properties (i.e. sufficient void volume within the nonwoven web) with the need to avoid that the lower ADS adds excessive bulk to the absorbent article, thus decreasing wearer comfort. The caliper of the lower ADS may be from 0.1 to 2.0 mm, or from 0.2 to 1.0 mm, as measured according to the test method set out herein below.

Also, for the lower ADS materials are desirable that exhibit good recovery after compression, given absorbent articles are often packed under relatively high compression. A material that initially had suitable characteristics for use as lower ADS, e.g. sufficient loftiness and void volume, may loose much of these beneficial properties upon compression in the packaging if its ability to recover is insufficient. This ability is reflected by the Z-Compliance Index and Percent Recovery Measurement Method set out below. A material suitable as lower ADS may have a Compliance Index greater than 4, preferably greater than 10, and a Percentage Recovery greater than 50, preferably greater than 60.

The basis weight of the lower ADS may be from 20 $g/m^2$ to 100 $g/m^2$, or from 20 $g/m^2$ to 80 $g/m^2$, or from 20 $g/m^2$ to 60 $g/m^2$.

The nonwoven comprised by or forming the lower ADS may have undergone mechanical deformation. Such mechanical deformation can contribute to the loft and openness of the nonwoven web, hence improving those properties of the nonwoven web which are desirable for use as lower ADS.

If the wearer- and/or garment facing surfaces of the lower ADS have a three-dimensional surface topography (as may, for example, be obtained by mechanical deformation), so-called "air pockets" may be obtained, especially if the lower ADS is in direct contact with layer (such as backsheet or lower substrate layer 46) having flat, two-dimensional surface topography. The three-dimensional surface of the lower ADS may only contact the adjacent layer (such as the backsheet or lower substrate layer 46) in areas protruding outwardly, leaving small gaps in the areas which are recessed. These gaps can increase wearer-comfort and soft feel of the absorbent article.

Also, it is desirable to have good air permeability of the lower ADS. As adding a lower ADS means adding an additional layer of material to the absorbent article, such additional layer should not excessively impact the overall air permeability of the absorbent article. By using a porous, relatively open structure of the nonwoven web of the lower ADS, such as a spunlace or air-through bonded nonwoven, suitable air permeability of the lower ADS can be obtained.

The lower acquisition and distribution system 60 may have an air permeability greater than 150 $m^3/m^2/min$, or from 200 $m^3/m^2/min$ to 800 $m^3/m^2/min$, as determined by the test method set out below.

The dry opacity of the lower acquisition system (i.e. the opacity measured in the dry lower ADS) may be relatively high to contribute to the overall opaque appearance of the absorbent article. Also, by having a lower ADS with a relatively high opacity, stains in the layer of absorbent material (e.g. from urine or feces) can be concealed from view, when looking at the backsheet of the absorbent article during use. The dry opacity of the lower ADS may be at least 25%, or at least 40%, or at least 50%, or at least 70% as measured according to the opacity test method set out below.

Bio-Sourced Materials

Components of the disposable absorbent article (i.e., diaper, pant, sanitary napkin, pantiliner, etc.) of the present invention can at least partially be comprised of bio-sourced content as described in US 2007/0219521A1 Hird et al published on Sep. 20, 2007, US 2011/0139658A1 Hird et al published on Jun. 16, 2011, US 2011/0139657A1 Hird et al published on Jun. 16, 2011, US 2011/0152812A1 Hird et al published on Jun. 23, 2011, US 2011/0139662A1 Hird et al published on Jun. 16, 2011, and US 2011/0139659A1 Hird et al published on Jun. 16, 2011. These components include, but are not limited to, topsheet nonwovens, backsheet films, backsheet nonwovens, barrier leg cuff nonwovens, superabsorbent material, upper and lower substrate layer, adhesives, fastener hooks, and fastener landing zone nonwovens and film based. For example, the upper and/or lower acquisition and distribution layer of the present invention may at least partially be comprised of bio-sourced content.

The disposable absorbent article component may comprise a bio-based content value from about 10% to about 100% using ASTM D6866-10, method B, in another embodiment, from about 25% to about 75%, and in yet another embodiment, from about 50% to about 60% using ASTM D6866-10, method B.

In order to apply the methodology of ASTM D6866-10 to determine the bio-based content of any disposable absorbent article component, a representative sample of the disposable absorbent article component must be obtained for testing. Thereto, the disposable absorbent article component may be ground into particulates less than about 20 mesh using known grinding methods (e.g., Wiley® mill), and a representative sample of suitable mass taken from the randomly mixed particles.

Test Methods

NMR MOUSE Test Method

The NMR MOUSE Test Method is used to quantify the liquid distribution in an absorbent article as a function of depth and after application of liquid insults at a position of interest in the absorbent article. The article is positioned in an apparatus that applies a constant pressure to the absorbent article, and while this pressure is applied, one or more insults of saline solution are applied to positions of interest in the absorbent article. The apparatus is additionally positioned with a low-field NMR instrument such that the instrument is capable of measuring liquid depth profiles of the absorbent article while under pressure. From these liquid depth profiles, depth zones of interest are defined, quantified, and reported. The general NMR test method and apparatus are also described in U.S. Pat. Nos. 10,371,652 and 10,365,237.

Figure 3:
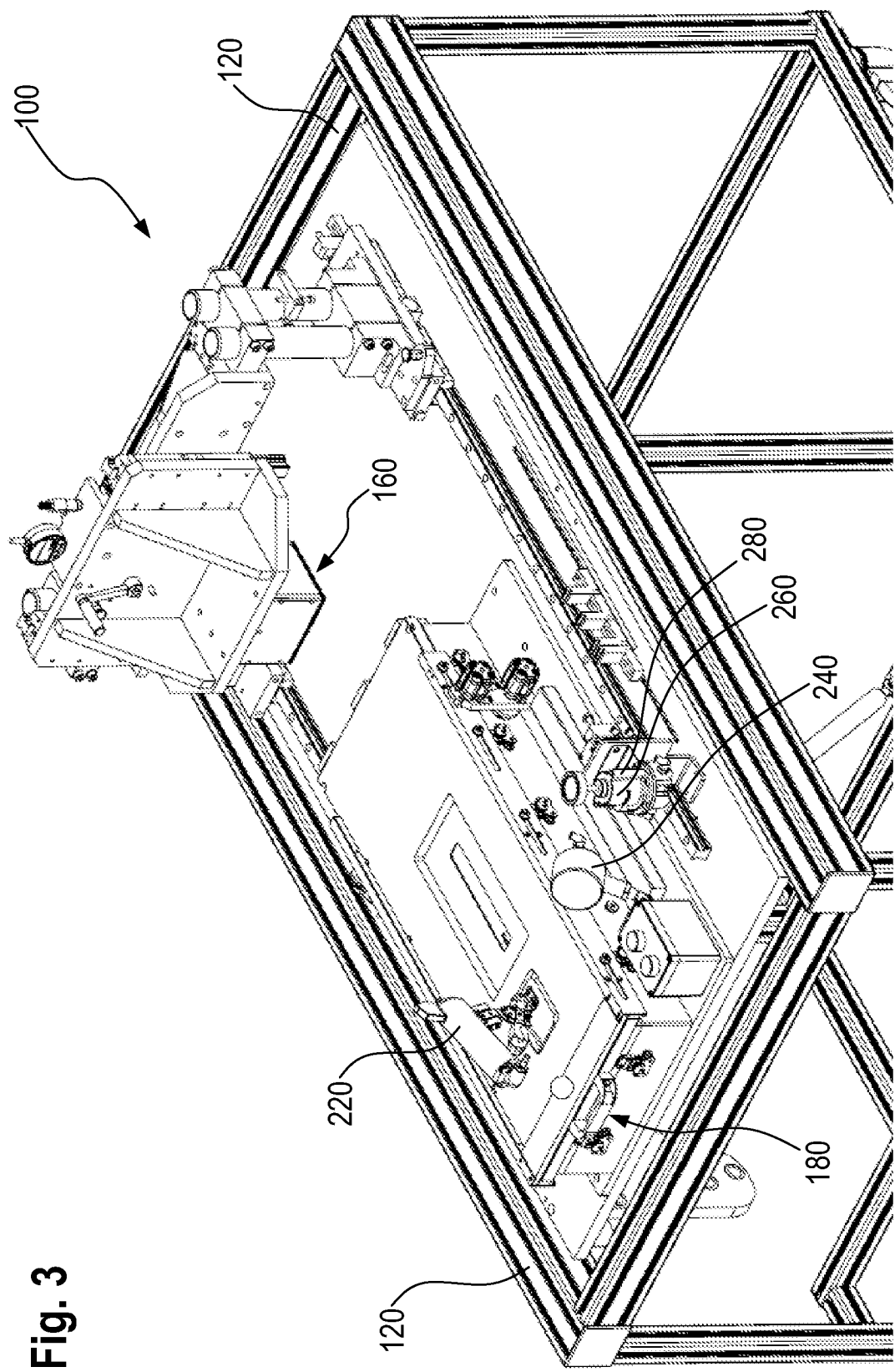
FIG. 3 is a perspective view of an exemplary device for the NMR MOUSE test method for analysis of fluid distribution in absorbent articles.
Figure 4:
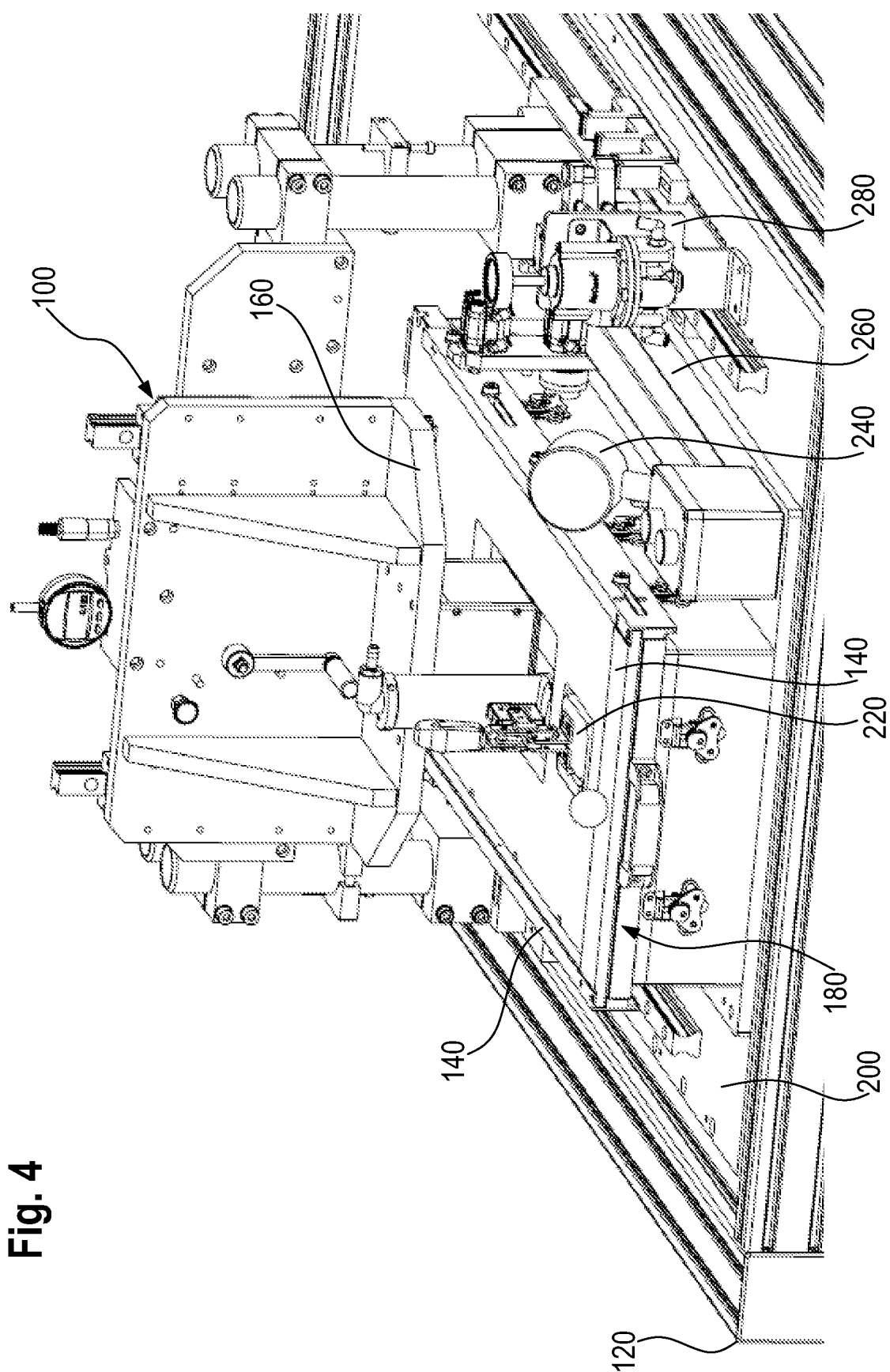
FIG. 4 is an alternative perspective view of the exemplary device of FIG. 3 for the NMR MOUSE test method for the analysis of fluid distribution in absorbent articles.

The device suitable for measuring a two-dimensional profile of the fluid distribution through a multi-layer absorbent article is shown in FIGS. 3-4. The device 100 comprises a frame 120, a pressure chamber 140, and an NMR MOUSE sensor 160. The NMR-MOUSE (Mobile Universal Surface Explorer) is a portable open NMR sensor equipped with a permanent magnet geometry that generates a highly uniform gradient perpendicular to the scanner surface (shown in FIG. 3). A flat sensitive volume of the specimen is excited and detected by a surface rf coil placed on top of the magnet at a position that defines the maximum penetration depth into the specimen. An exemplary instrument is the Profile NMR-MOUSE model PM10 from Magritek Inc., San Diego, CA. Requirements for the NMR-MOUSE to achieve a 50 µm resolution in the z-direction, are a measuring frequency of 14.07 MHz, a maximum measuring depth of 10 mm, a static gradient of 13 T/m, and a sensitive volume (x-y dimension) of 19 mm² by 19 mm². Before the instrument can be used, perform phasing adjustment, check resonance frequency and check external noise level as per the manufacturer's instruction. All measurements are conducted in a room controlled at 23° C.±2° C. and about 50%±2% relative humidity.

The pressure chamber 140 is formed from a conformable and pressurizable surface such as exemplary bladder assembly 180 and a top plate assembly 200 which includes a deposition assembly 220.

The bladder assembly 180 is constructed of 12.7 mm glass fiber reinforced epoxy (DIN 7735/HGW 2372.4) to provide an overall dimension of 80 cm long by 30 cm wide by 5 cm tall. A manometer 240 is provided for the measurement of the pressure inside the pressure chamber 140. A pressure gauge 260 is provided to regulate the introduction of air into the pressure chamber 140 and can be positionably installed through access holes cooperatively disposed upon the right side of pressure chamber 140.

Figure 5:
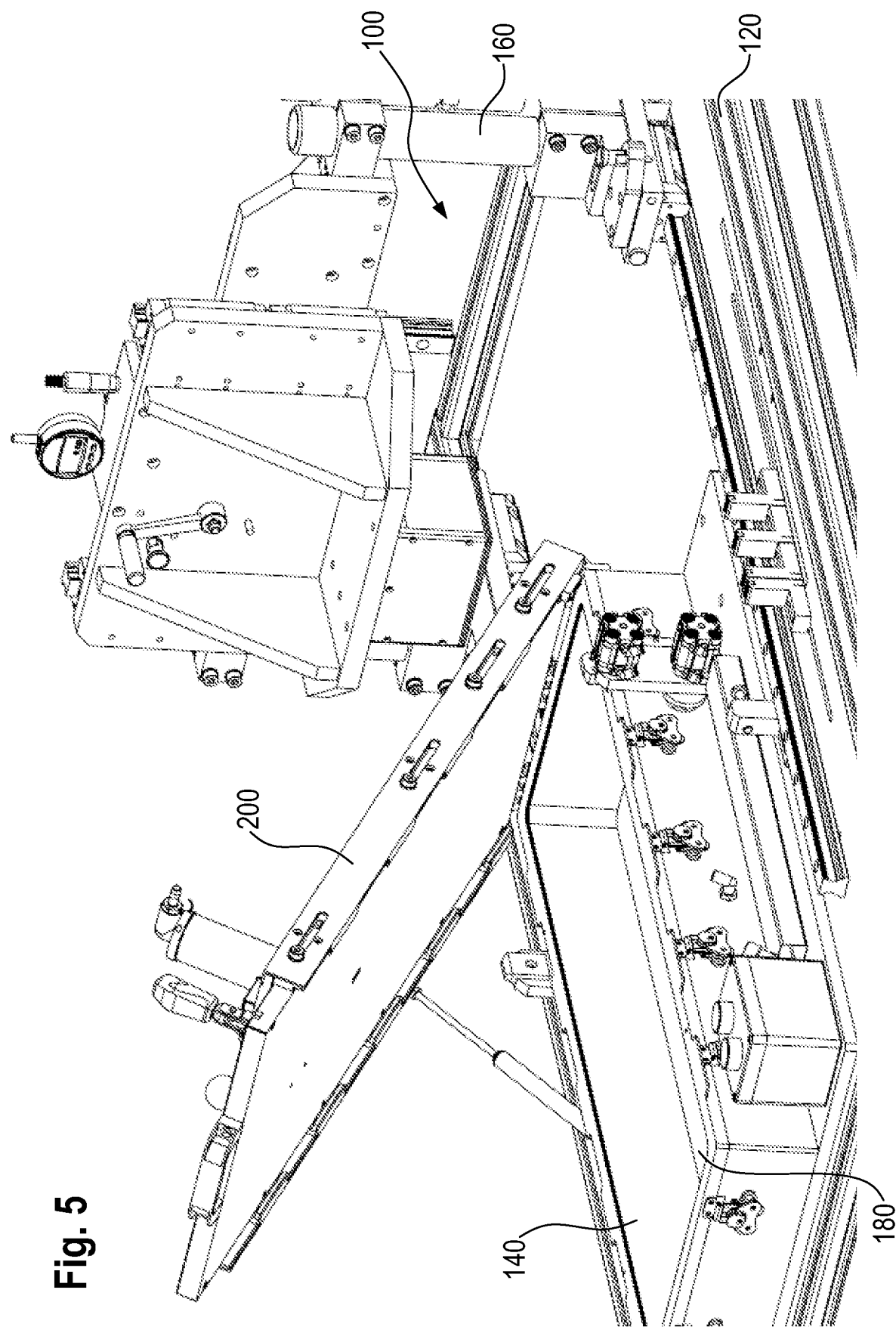
FIG. 5 is an alternative perspective view of the exemplary device of FIG. 3 for the NMR MOUSE test method for the analysis of fluid distribution in absorbent articles where the top plate and bladder assembly of the pressure chamber are separated for sample insertion.

FIG. 5 illustrates the device 100 showing the separable and displaceable nature of the top plate assembly 200 relative to the bladder assembly 180 of pressure chamber 140 as well as frame 120. As shown in FIG. 5, the top plate assembly 200 can be attached to bladder assembly 180 and rotated about a longitudinal axis of attachment of top plate assembly 200 to the bladder assembly 180 at an angle, γ, to facilitate user access to that region of the internal portion of pressure chamber 140 disposed between top plate assembly 200 and bladder assembly 180.

Figure 6:
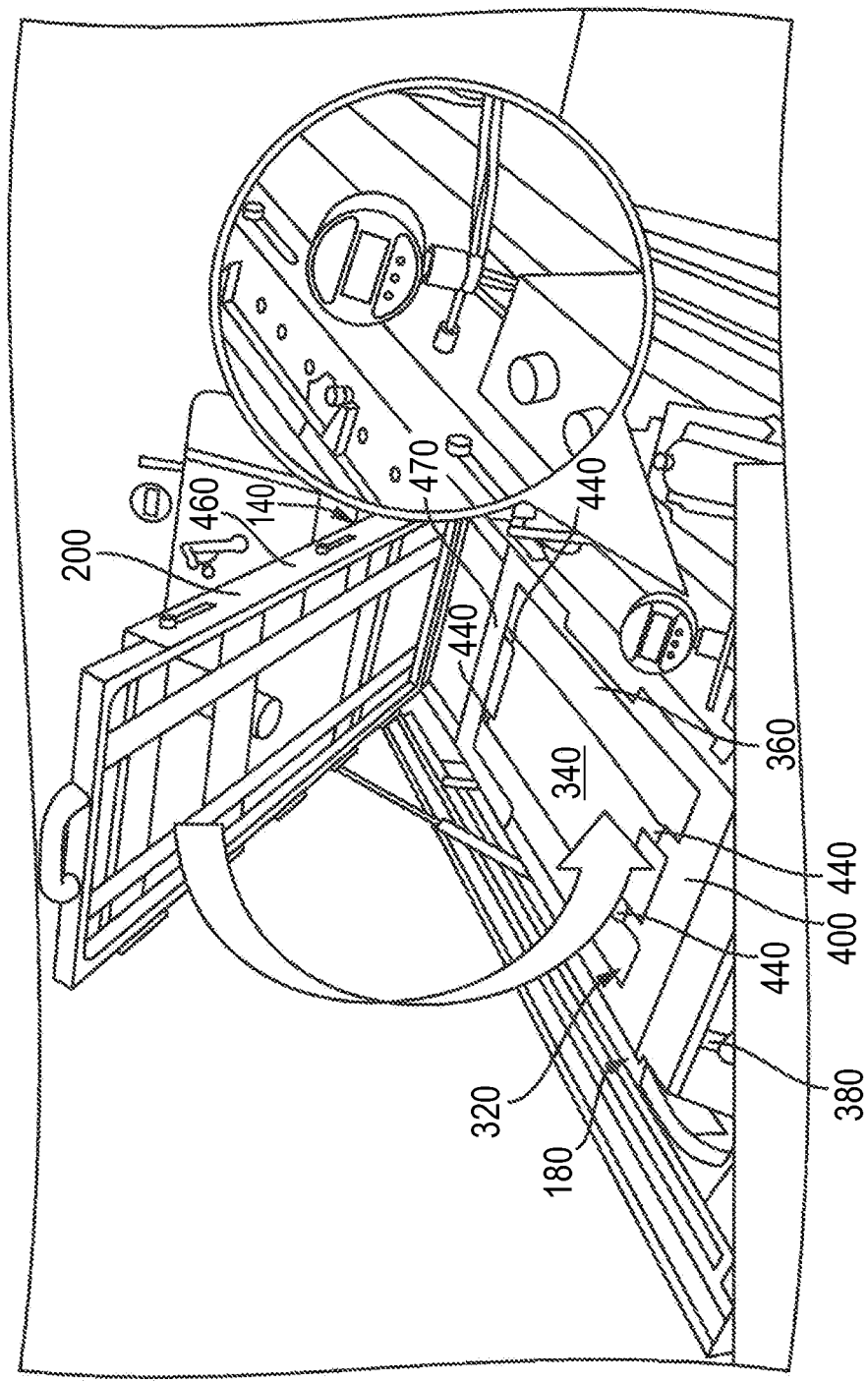
FIG. 6 is yet another alternative perspective view of the exemplary device of FIG. 3 for the NMR MOUSE test method for the analysis of fluid distribution in absorbent articles where the top plate and bladder assembly of the pressure chamber are separated and a bladder and sample are inserted therein.

As shown in FIG. 6, the bladder assembly 180 of pressure chamber 140 can be provided with a bladder 320. Bladder 320 can be cooperatively associated and sealingly engaged to bladder assembly 180 of pressure chamber 140 by draping the bladder 320 over the top of bladder assembly 180 with enough slack to provide that the bladder 320 touches the bottom of bladder assembly 180 at its center point. The bladder 320 can be provided as a 50 mm×100 mm piece of silicone film having a thickness of 0.02 inches and a Shore A durometer value of 20. An exemplary material suitable for use as bladder 320 is available as Part#86435K85 from McMaster-Carr, Cleveland, OH.

Preferably, a secondary frame 360, having a fitting flange is fitted over the top of the bladder 320 and secured to the bladder assembly 180 with clamps 380. When bladder 320 is sealably secured to bladder assembly 320, it is preferred that the bladder/bladder assembly 320 combination assembly be leak free at a pressure of 0.3 psi.

A front sample support 400 and back sample support 420 can be used to anchor a sample 340 or article to be measured by the device 100 relative to bladder assembly 180. As required, the sample 340 or article can be attached to the front 400 and back 420 sample supports by attachment means 440. Such attachment can be provided by an end user as would be determined by one of skill in the art. Attachment means 440 can be provided as an adhesive tape fastening system, mechanical "hook" fasteners, adhesive attachment systems, combinations thereof, and the like. Front sample support 400 and back sample support 420 can be adjusted as may be required along the length (i.e., y-axis) of the secondary frame 360. The adjustment of front sample support 400 and back sample support relative to secondary frame 360 can be provided as a pin and hole system and the like as would be understood by one of skill in the art for the accommodation of differently sized absorbent articles to correctly align the loading point of the absorbent article.

The top plate assembly 200 can be provided by an appropriately sized Glass fiber reinforced epoxy (DIN 7735/HGW 2372.4) piece reinforced with a support frame 460 to enhance rigidity. It is preferred that the portion of top plate assembly 200 disposed proximate to the sample 34 that is disposed upon bladder 320 and proximate to the area that NMR sensor 160 will operate be essentially transparent to NMR-MOUSE radiation.

Figure 7:
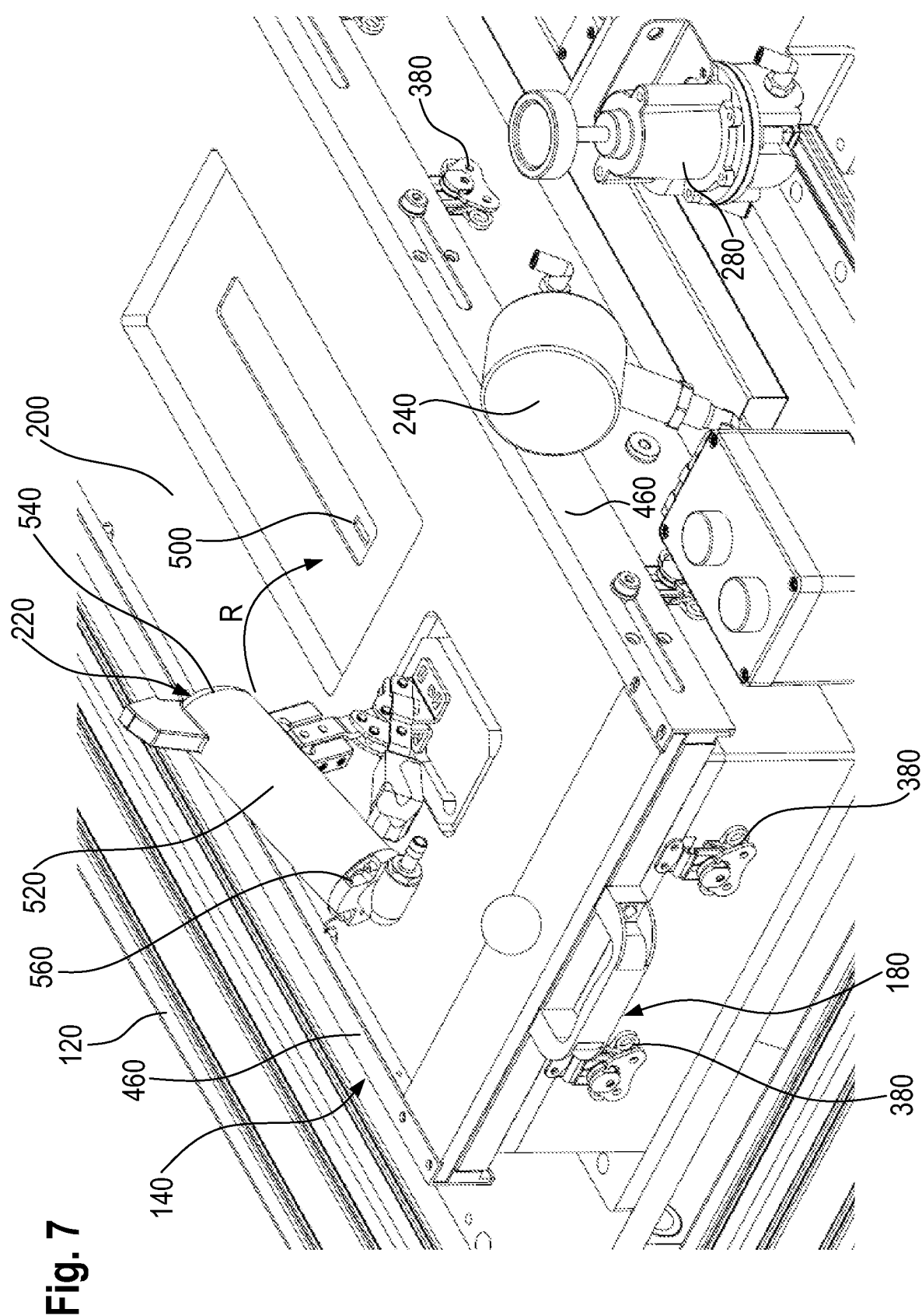
FIG. 7 is a perspective view of an exemplary deposition assembly for the NMR MOUSE test method suitable for cooperative engagement with the top plate of an exemplary pressure chamber.
Figure 8:
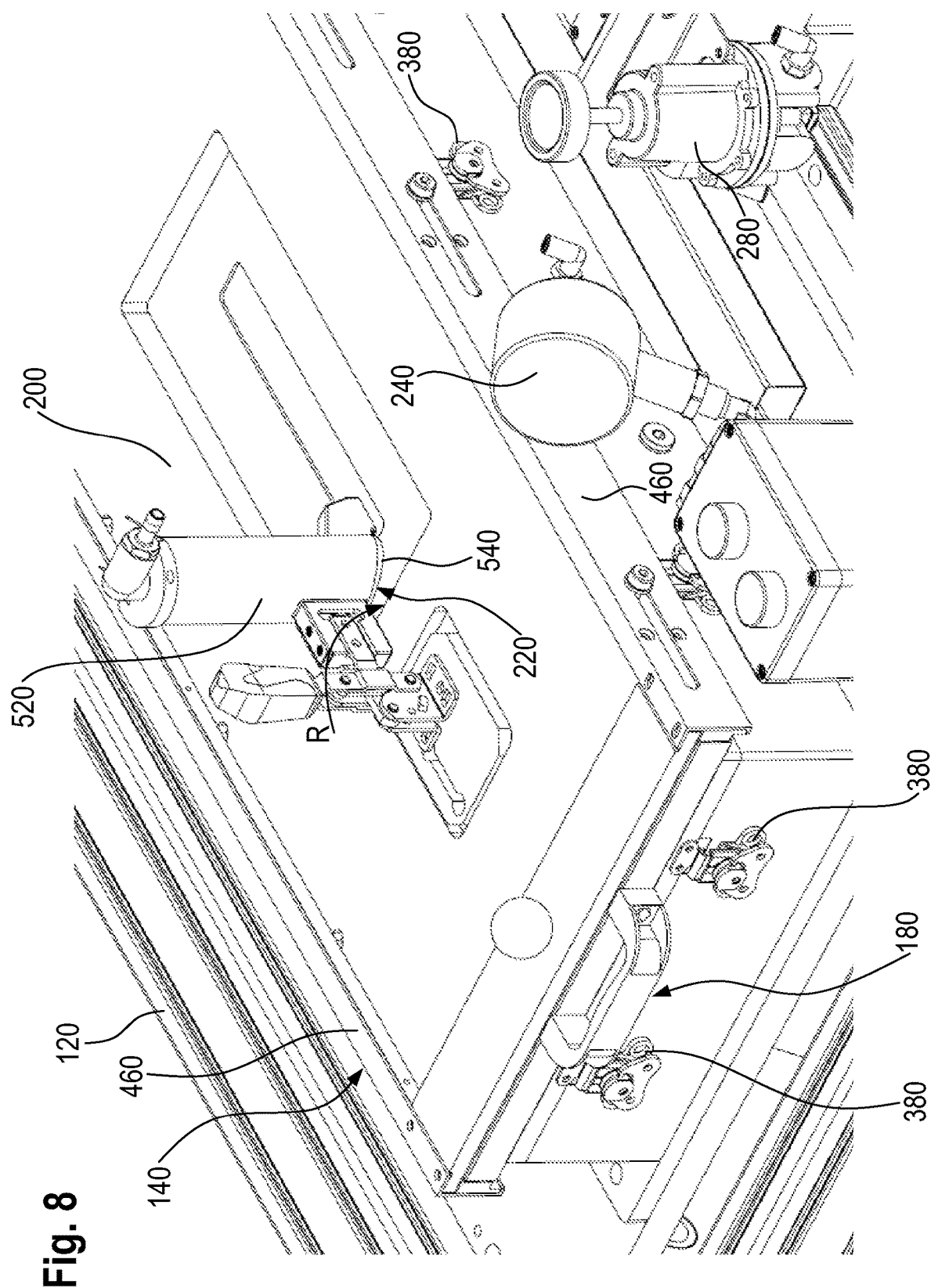
FIG. 8 is a perspective view of an exemplary deposition assembly in cooperative engagement with the insult application aperture disposed within the top plate of an exemplary pressure chamber.

As shown in FIGS. 7-8, deposition assembly 220 can be disposed upon a surface of top plate assembly 200. Deposition assembly 220 can facilitate the deposition of an insult upon sample 340 disposed upon bladder 320 disposed within pressure chamber 140. Deposition assembly 220 is preferably rotatable about an axis, R, to facilitate the placement and displacement of deposition assembly into, and out of, contacting engagement with insult application aperture 500 disposed within top plate assembly 200. Deposition assembly 220 is disposed so as to be located centrally relative to top plate assembly 200 and cooperatively aligned with insult application aperture 500.

One of skill in the art will appreciate that a suitable deposition assembly 220 can be constructed from a material that is transparent to NMR-level RF. The deposition assembly 220 is constructed with PA12-GF as cylinder and opening of 1 cm by 2 cm. When deposition assembly 220 is cooperatively aligned with insult application aperture 500, it is preferred that deposition assembly 220 be inserted through the top plate assembly 200, through insult application aperture 500 so that the contacting edge 540 of deposition assembly 220 is cooperatively aligned with the surface of top plate assembly 200 that is in contacting engagement with sample 340 disposed within pressure chamber 140.

The unique procedure outlined infra can facilitate the: a) measurement of a sample 340 profile from top side and b) measurement of a sample 340 profile from bottom side. In other words, the described process can facilitate the measurement of the liquid distribution inside a sample 340 (e.g., a absorbent article) quantitatively within very short time.

Samples 340 are conditioned at 23° C.±2° C. and about 50%±2% relative humidity for twelve (12) hours prior to testing. A sample 340 (e.g., an absorbent article) is prepared by placing the sample 340 flat onto a lab bench and identifying the intersection of the longitudinal and lateral centerlines of the sample 340. For a sample 340 provided as a absorbent article in the form of a pant, any cuffs or waistbands are removed so as not to damage the top sheet or layer of absorbent material, lower and, if present, upper acquisition and distribution system, backsheet, and, if present, upper and lower substrate layers 45, 46, of the sample 340. The sample 340 or article can be attached to the front 400 and back 420 sample supports of secondary frame 360 by attachment means 440. Attachment means 440 can be provided as either adhesive tape or mechanical "hook" fasteners with the topsheet or backsheet of sample 340 facing upward (i.e., the absorbent article sample 340 is positioned so that the topsheet or backsheet of the absorbent article is disposed proximate to NMR sensor 160).

Sample 340 is placed in a manner so that just the chassis (e.g. portions of topsheet and backsheet extending outwardly from the layer of absorbent material) and not the layer of absorbent material of sample 340 overlays secondary frame 360. The front 400 and back 420 sample supports are attached to the secondary frame 360 so that the absorbent article will be centered longitudinally and laterally relative to insult application aperture 500 when the top plate assembly 200 has been closed relative to bladder assembly 180. The back end of the sample 340 is secured to back 420 sample support of secondary frame 360 by either adhesive tape or mechanical "hook" fasteners, once again ensuring that only the chassis and not the absorptive core overlays the application aperture 500. The back sample support 420 is then attached to the secondary frame 360 so that the sample 340 is taut but not stretched. The top plate assembly 200 is closed and fastenably attached to bladder assembly 180 to form pressure chamber 140. The bladder of pressure chamber 140 is inflated up to 0.30 psi. The loading point for different diaper sizes are defined in the table below:

| Length of absorbent article | ≤450 mm | >450 mm |
|---|---|---|
| Loading point - Distance from front edge of layer of absorbent material (mm) | 138 | 102 |
| Gush Volume (ml) | 40 | 75 |

In other words, preparation of the sample 340 for analysis by the device 100 incorporating NMR sensor 160 can be summarized as follows:
1. Prepare the sample 340 (e.g., remove/cut the cuffs, determine loading point, etc.).
2. Move the NMR sensor 160 away from the insult application aperture 500 disposed within top plate assembly 200 relative to a position disposed distal from insult application aperture 500.
3. Open the glass cover by disassociating top plate assembly 200 of pressure chamber 140 from bladder assembly 180.
4. Insert the sample 340 (absorbent article) by attaching the sample 340 to front sample support 400 and back sample support 420 to anchor the sample 340 to be measured by the device 100 relative to bladder assembly 180 by attachment means 440.
5. Close top plate assembly 200 by cooperatively associating top plate assembly 200 of pressure chamber 140 to bladder assembly 180.
6. Apply and regulate the pressure applied to bladder 320 disposed within bladder assembly 180 disposed within pressure chamber 140 to the desired value (here 0.3 psi).

In principle, the process for the analysis and mapping of fluid inside a sample 340 is based on wetting of the examined absorbent article with series of liquid insults of the given flow parameters and evaluating fluid distribution inside the absorbent article sample 340. Due to application of pressure to the bottom of the absorbent article sample 340, absorbent article 340 swelling is directed away from NMR sensor 160. Therefore, distance between the absorbent article 340 surface and the NMR sensor 160 is always kept constant and does not change with different experimental conditions.

Liquid Application Procedure

Figure 9:
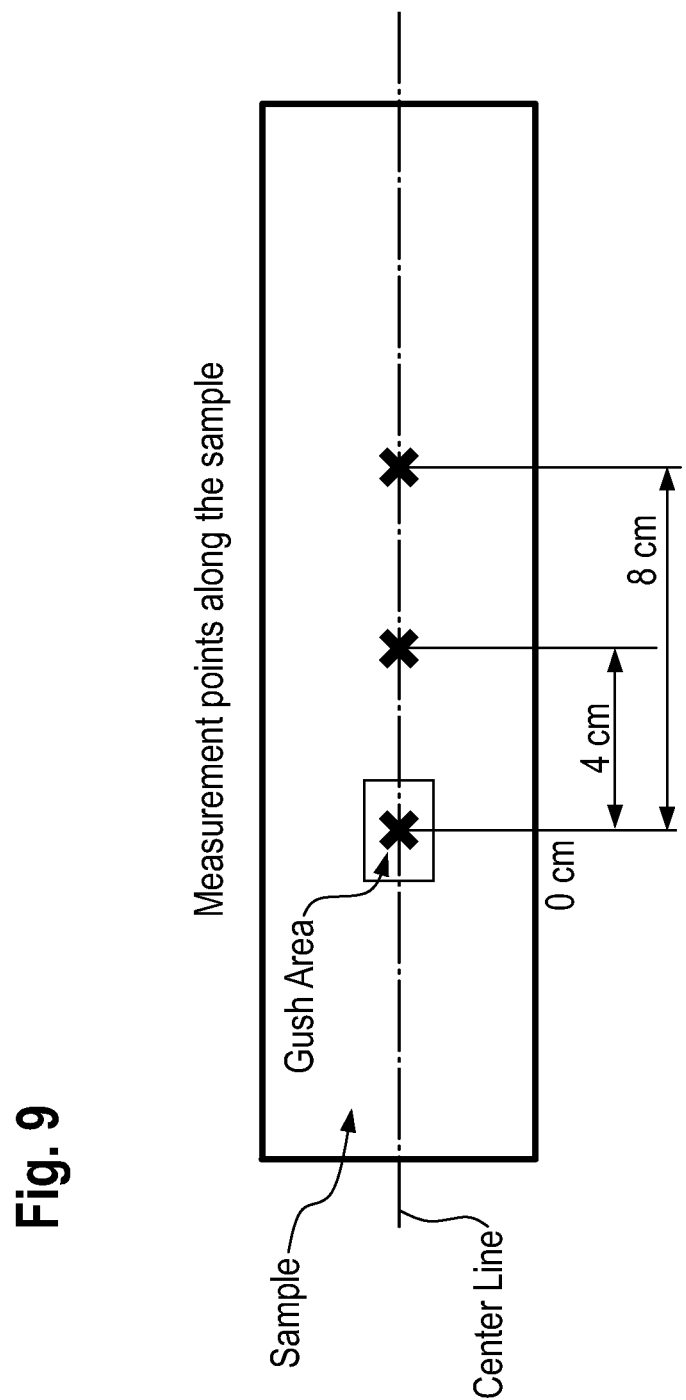
FIG. 9 shows an exemplary schematic top view for the three profiling spots (x) used for the NMR MOUSE test method.
Figure 10:
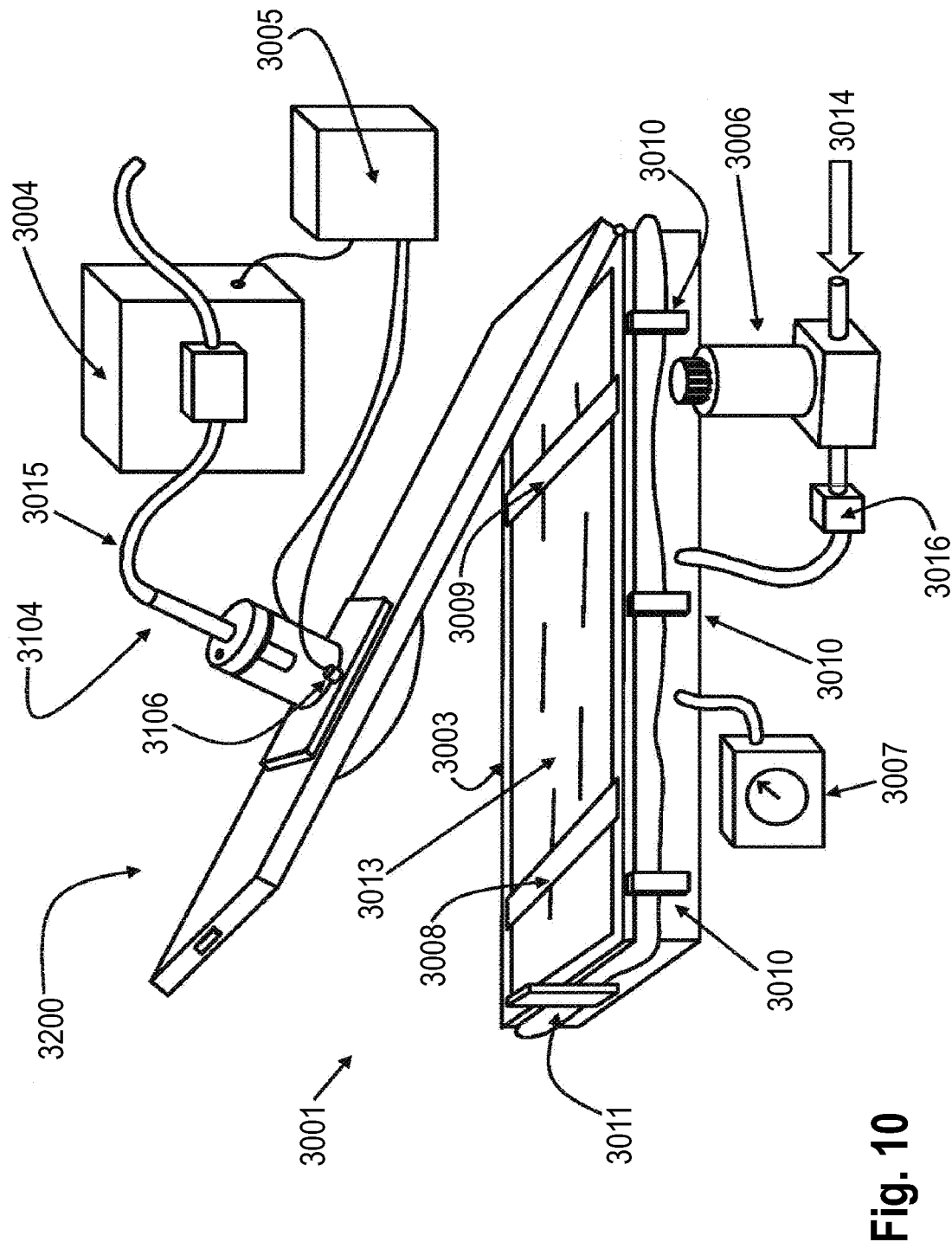
FIG. 10 illustrates an apparatus used in the Modified Fluid Acquisition Test.

Two subsequent gushes of insult (see gush volume/absorbent article length table) are used with 300 seconds±5 seconds breaks in between consecutive insults. As shown in FIG. 9, when measurements of an insulted sample 340 are conducted, the NMR sensor 160 is preferably positioned a known distance from the insult/gush center relative to insult application aperture 500 and at given height from the sample 340 surface.

The test solution is prepared: 0.9% w/v saline solution prepared as 9.0 g of NaCl diluted to 1 L deionized water. A solution 2 mM/L of Diethylenetriaminepentaacetic acid gadolinium (III) dihydrogen salt (PubChem Substance ID 24863829,381667, available from Sigma Aldrich) is added. After addition the solutions are stirred using a shaker at 160 rpm for one hour until all crystals are dissolved. Do not use a magnet bar to stir the solution. Afterwards the solutions are checked to assure no visible undissolved crystals remain. The solution is prepared 10 hours prior to use. The process of liquid application can be summarized as follows:
1. Position NMR sensor 160 proximate to insult application aperture 500 disposed within top plate assembly 200 horizontally and proximate to insult/gush area; position the NMR sensor 160 as required from the geographic center of the insult/gush center.
2. Position NMR sensor 160 3500 μm from the top surface of sample 340 contactingly engaged with top plate assembly 200 of bladder assembly 180.
3. Dispose insult fluid and contrast agent within deposition assembly 220.
4. Position deposition assembly 220 relative to insult application aperture 500 and the top surface of sample 340.
5. Insult top surface of sample 340 with at least a portion of insult fluid and contrast agent through deposition assembly 220.
6. Apply series of insult/gushes with the predefined parameters (e.g., two injections of 40 mL, flow rate 10 mL/sec, 300 seconds±5 seconds break between the gushes).

Profile Testing Process

Profiling testing is started 300 seconds±5 seconds after a liquid application. Profiling gives signal response versus sample depth and it aims to screen the sample within the given measurement range (800 μm from top and bottom). This way liquid distribution across different sample layers can be quantified. Profiling is conducted in different spots along the sample length (at the loading-point, 4 cm and 8 cm away from the loading-point towards the back), 2-D liquid distribution inside the sample can be finally obtained by combining the obtained results. An exemplary schematic top view for three profiling spots (at loading point and 4 and 8 cm away from loading point and on symmetry line) used in the study is shown in FIG. 9.

Program the NMR-MOUSE for a Carr-Purcell-Meiboom-Gill (CPMG) pulse sequence consisting of a 90°x-pulse follow by a refocusing pulse of 180°y-pulse using the following conditions:
Repetition Time=500 ms
Number of Scans=8
Number of Echoes=8
Resolution=50 μm
Step Size=−50 μm
Pulse Length=7.5 μs
Echo Time=90 μs
Echo Shift=1 μs The Rx phase of the NMR signal is optimized during the phase adjustment as described by the vendor to maximize the real part of the NMR signal, which is used for data processing. A value of 195° was applied for our experiments. However, the optimal value may differ depending on the NMR instrument used, and hence the Rx phase should be optimized as described by the vendor. Pulse length for a 90° pulse depends on measurement depth which here is 6 mm and was determined to be 7.5 μs based on the optimization procedure described by the vendor. If necessary, the depth can be adjusted using a spacer.

In other words, the process for conducting the profile testing process of the sample 340 for analysis by the device 100 incorporating NMR sensor 160 can be summarized as follows:
1. Translate the NMR sensor 160 to its top position distal from sample 340 disposed within bladder assembly 180, reaching an outermost vertical position.
2. Move the NMR sensor 160 to an outermost horizontal position disposed distal from insult application aperture 500.
3. Remove the deposition assembly 220 from contacting engagement with insult application aperture 500.
4. Move the NMR sensor 160 horizontally (i.e., y-direction) relative to insult application aperture 500 so NMR sensor 160 center overlaps insult application aperture 500 center (i.e., position 0 cm (i.e. at loading point)).
5. Run profiling experiment (scanning range 0-800 µm, step size 50 µm).
6. Set the NMR sensor 160 to an initial position (800 µm) relative to the top of sample 340 disposed within bladder assembly 18 and lower its position incrementally 50 µm as required.
7. When the experiment is completed, translate the NMR sensor 160 to the outermost vertical (i.e., Z-direction) position.
8. Repeat steps 4-7 while placing the sensor at positions 4 and 8 cm from the loading point.
9. For measuring the specimen from back sheet side, remove the specimen and attach it to the bladder with back sheet facing up and repeat steps 1-8.

At the conclusion of testing, the sample 34 can be extricated from the device 100 as follows:
1. Translate NMR sensor 160 vertically (i.e., Z-direction) to an outermost position.
2. Translate NMR sensor 160 horizontally (i.e., y-direction) to an outermost horizontal position.
3. Release pressure applied to bladder 320.
4. Disassociate top plate assembly 200 of pressure chamber 14 from bladder assembly 180.
5. Remove the sample 340 from pressure chamber 140.
6. Close top plate assembly 200 by cooperatively associating top plate assembly 200 of pressure chamber 140 to bladder assembly 180.

It should be noted that with the regular NMR-MOUSE the distance between the RF Coil of the NMR sensor 160 and the top layer of the sample 340 disposed within bladder assembly 180 may not be constant during the absorptive process due to swelling of the sample 340. Use of the bladder assembly 180 in conjunction with NMR sensor 160 provided as device 100 was found to provide a measurement by NMR sensor 160 independent of any swelling experienced by sample 340 as the sample 340 can swell away from the sensitive slice currently being scanned by NMR sensor 160.

In order to translate signal amplitude into quantitative information on detected liquid volumes, the raw calibration data for profiling needs to be correlated with the actual volume of 0.9% saline. Calibration is done with the use of liquid mixture of the experimental wetting solution (0.9% saline) and deuterium oxide ($D_2O$). Regarding to the fact that NMR testing requires contrast agent application, both solutions should be additionally mixed with 2 mM/L of Diethylenetriaminepentaacetic acid gadolinium (III) dihydrogen salt (PubChem Substance ID 24863829,381667, available from Sigma Aldrich) contrast agent in advance. For preparing the calibration solutions, mix the $D_2O$ solution with the Saline solution to receive: 0%, 20%, 80% and 100% of 0.9% saline solution with contrast agent. Shake the mixtures and leave them for at least 12 hours prior testing as to ensure proper mixing of the components. Add the solutions in glass beaker with area bigger than NMR sensor area and with thickness less than 1 mm such that volume being scanned by the NMR device is entirely in the measurement range. Perform profiling measurements in a range below the surface of solutions. Repeat the procedure for other calibration mixtures as to cover all different ratio options. Calculate the area under the graph for each measured case using the formula below:

$$\text{Area} = \sum_{i=1}^{n} \frac{X_{i+1} - X_i}{2} \times (S_{i+1} + S_i) \quad (1)$$

Where X is the depth in µm and S is the NMR Signal, n is the number of the data points depending on the measurement depth and resolution. Calculate the 0.9% saline volume for each of the option, regarding the overall scanning range and mixture ratio (i. e. saline content×sensor area×scanning range). Calculate the measured volume (VM) based on the total amount of volume (VT) in profiling region based on the equations below:

Sensor Area: SA=3.61 [$cm^2$]

Profiling depth: D [mm]

Total volume: VT=SA×D×100 [µL]

Saline Ratio (1−$D_2O$ ratio):R %

Measured volume: VM=VT×R  (2)

Prepare calibration graph of the given data set and apply linear fit as to obtain calibration curve equation. Subtract area under the graph for 100% $D_2O$ from each option containing $D_2O$ in mixture. In the assumed case, the profiling depth reaches 1.5 mm, while the area of the sensor covers 3.61 $cm^2$ (sensor 1.9×1.9 cm). The total volume covered by the profiling results then in 542 µL for 0% $D_2O$ solution. If the miscibility of $D_2O$ and a desired test solution does not match, perform a one-point calibration (100% solution without $D_2O$).

While reviewing the profile data, the NMR signal is related to the area under the curve in the signal vs. position graph. An area vs. liquid volume correlation may be obtained by integrated area for each of the examined saline content case and knowing the saline volumes. A calibration curve for profiling can be derived by graphically reviewing the linear trend. Limits of detection and quantification (3σ and 9σ respectively) can be established from the signal noise standard deviation for a sample containing 100% $D_2O$. The raw data measured by NMR-MOUSE (signal amplitude [A.U.] vs position [µm]) need to be converted into area under the graph values (Area) using the equation (1) for the first zone corresponding to 800 µm starting from and including the topsheet and extending towards the backsheet, and a second zone corresponding to 800 µm starting from and including the backsheet and extending towards the topsheet. The area under the graph values (Area) are also calculated for the profiles measured at 4 cm and 8 cm away from the loading point (FIG. 9) using equation (1). Only then the Area may be converted into liquid volume using the calibration curve and the linear fit using the equation (3).

Volume=(Area×m)+b  (3)

Where m is the slope of the calibration curve and b is the intercept. The Volume (=amount of liquid) for the first zone and second zone is calculated using equation (3) for the profiles at 0 cm (=at loading point), 4 cm and 8 cm from loading point (loading point is defined based on diaper length) and reported to the nearest 1 μL.

In like fashion, run a total of three (3) replicates for each absorbent article to be evaluated. Calculate and report the Volume (=amount of liquid) for the first and second zone and at the three locations (i.e. 0 cm (=at loading point), and 4 cm and 8 cm away from loading point) and for the sum of the three location for each product as the arithmetic mean of the replicates to the nearest 1 μL.

Air-Permeability Test Method

All measurements are performed in a laboratory maintained at 23±2° C. and 50±2% relative humidity and test specimens are conditioned in this environment for at least 2 hours prior to testing.

The Air Permeability of a substrate is determined according to INDA/EDANA Nonwovens Standard Procedures NWSP 070.1.R0 (15) making use of a Textest FX3300 (Textest Instruments, Schwerzenbach, Switzerland) air permeability tester or equivalent. A circular test head with an area of 20 cm$^2$ is used, and while a fixed pressure of 200 Pa is maintained across the lower ADS specimen, air flow through the lower ADS is measured in cubic meter per square meter per minute (m$^3$/m$^2$/min). If possible, measurements are made on the lower ADS before it is integrated in an absorbent article. If this is not possible, care should be exerted when excising the lower ADS from the product not to impart any contamination or distortion to the test sample layer during the removal of the material from other layers (using cryogenic spray, such as Cyto-Freeze, Control Company, Houston, Texas, if needed). Five rectangular specimens of the lower ADS are taken such that each specimen center corresponds to the position of the loading point on the lower ADS and such that the length and width of each specimen are greater than the smallest dimension of the circular head. The lower ADS specimen is placed under the test head such that the center of the lower ADS specimen is matching the center of the test head. The five lower ADS specimens are analyzed in this way, and the air permeability of each is recorded in m$^3$/m$^2$/min to the nearest 1 m$^3$/m$^2$/min. The arithmetic mean of the individual specimen results is calculated and reported as the Air Permeability in units m$^3$/m$^2$/min to the nearest 1 m$^3$/m$^2$/min.

Opacity Test Method

Opacity by contrast ratio measurements are made using a 0°/45° spectrophotometer suitable for making standard CIE L*a*b* color measurements such as the Hunter ColorFlex EZ Spectrophotometer (Hunter Associates Laboratory Inc., Reston, Virginia, USA) or equivalent. The diameter of the instrument's measurement port is 30 mm. Analyses are performed in a room controlled at about 23° C.±2C.° and 50%±2% relative humidity.

The instrument is calibrated per the vender instructions using standard black and white tiles provided by the instrument vendor. After calibration, the Y value of a standard white tile is measured and compared to its true value. The specified true Y value is of the standard white tile is typically in the range of 83 to 85, and the difference from true value should be 0.5 or less. The spectrophotometer is set to use the CIE XYZ color space, with a D65 standard illumination and 10° observer.

If possible, measurements are made on the lower ADS before it is integrated in an absorbent article. If this is not possible, care should be exerted when excising the lower ADS from the product not to impart any contamination or distortion to the test sample layer during the removal of the material from other layers (using cryogenic spray, such as Cyto-Freeze, Control Company, Houston, Texas, if needed). Five rectangular specimens of the lower ADS are taken such that each specimen center corresponds to the position of the loading point on the lower ADS and such that the length and width of each specimen are greater than the smallest dimension of the head.

The lower ADS specimen is positioned flat against the instrument with the outward facing surface toward the spectrophotometer's measurement port and the center of the lower ADS specimen (which corresponds to the loading point of the lower ADS) is matching with the center of the port. The specimen is further positioned such that no tears, holes or apertures are within the measurement port. The white standard tile is placed onto the opposing surface of the specimen such that it completely covers the portion of the specimen over the measurement port. A reading of XYZ values is taken, and each is recorded to the nearest 0.01. Without moving the specimen, the white plate is removed and replaced with the black standard plate. A second reading of XYZ values is taken and each is recorded to the nearest 0.01.

Opacity is calculated by dividing the Y value measured using the black tile as backing, divided by the Y value measured using the white tile as backing, then multiplying the ratio by 100.

$$\text{Opacity } [\%] = \frac{Y \text{ reading over black tile}}{Y \text{ reading over white tile}} \times 100\%$$

The five lower ADS specimens are analyzed in this way, and the Opacity of each is recorded. The arithmetic mean of the individual specimen results is calculated and reported as the Opacity in percentage to the nearest 1%.

Caliper Test Method

The Caliper of the lower ADS is determined using the Caliper Test Method. In the Caliper Test Method, two flat, parallel surfaces are used to apply unidirectional pressure to both sides of a substrate specimen, and the resulting separation between the parallel surfaces is measured. All measurements are performed in a laboratory maintained at 23±2° C. and 50±2% relative humidity and test specimens are conditioned in this environment for at least 2 hours prior to testing.

Two parallel circular surfaces of 5.6 cm diameter are oriented horizontally. If possible, measurements are made on the lower ADS before it is integrated in an absorbent article. If this is not possible, care should be exerted when excising the lower ADS from the product not to impart any contamination or distortion to the test sample layer during the removal of the material from other layers (using cryogenic spray, such as Cyto-Freeze, Control Company, Houston, Texas, if needed). Five equivalent rectangular specimens are taken from the lower ADS of five products such that each specimen center corresponds to the position of the loading point on the lower ADS and such that the length and width of each specimen is greater than 5.6 cm. A specimen is then placed between the two parallel circular surfaces so that it completely covers each of the parallel surface and such that the center of the lower ADS specimen is matching with the center of the parallel circular surfaces.

The parallel surfaces are then brought together at a rate of 3.0±1.0 mm/s until a pressure of 0.3 psi (2.1 kPa) is achieved, and the separation between the plates is measured and recorded to the nearest 0.01 mm within 2 seconds. The arithmetic mean of the plate separation of the 5 individual replicate specimens is calculated and reported as the Caliper of the substrate under 2.1 kPa in units of millimeters (mm) to the nearest 0.01 mm.

One suitable example of apparatus for use in the Caliper Method is a Mitutoyo Digimatic Series 543 ID-C digital indicator (Mitutoyo America Corp., Aurora, Illinois, USA), or equivalent, fitted with a circular flat "foot" at the end of the moving shaft of the indicator gauge. The indicator is mounted on a horizontal granite base such that the shaft of the indicator gauge is oriented vertically and the plane of the circular foot is parallel to the granite base. The circular foot is sized and weighted such that the gravitational force associated with the mass of the foot and the indicator shaft together divided by the area of the circular foot constitutes 0.3 psi of downward pressure from the circular foot on the granite base. Specimens at least as large as the circular foot are analyzed between the circular foot and granite base.

Horizontal Bending Drop at 100 mm Measurement Method

Principle: this method measures the ability of a nonwoven web to bend under his own weight (sometimes designated as "drapability"). The measurement principle is to hang a length of 100 mm of the material over a sharp 90° edge and measure the vertical drop of this length of the material under its own weight, expressed in mm. This vertical drop is illustrated as reference number 1 in FIG. 15.

Figure 15:
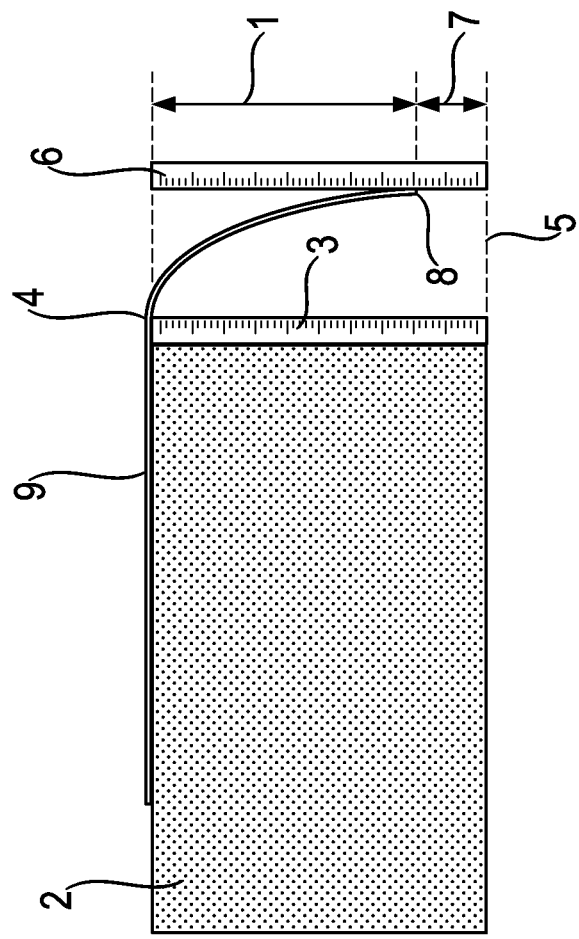
FIG. 15 shows a schematic setup for conducting the Horizontal Bending Drop Test.

Apparatus: the setup for conducting the measurement is schematically shown in FIG. 15 and comprises:

(i) a flat support box 2 made of any suitable material such as polycarbonate (e.g. Lexan®) about 400 mm long, about 200 mm wide and a height 3 of exactly 140 mm, with at least one of its top edge 4 in the width direction having a sharp 90 degree angle. The box 1 is positioned on a suitable flat surface 5, such as a lab bench;

(ii) a movable vertical metal ruler 6, having a stable horizontal foot, and calibrated so that its zero corresponds to the flat surface 5 on which the box is disposed. The movable vertical metal ruler is used to measure the distance 7 of the hanging edge 8 of the material specimen 9 to the flat surface.

Procedure: Measurements are performed at 23° C.±2° C. and 50%±2% RH. All samples should be kept at least 24 hours in these conditions to equilibrate before conducting the tests, unless indicated otherwise. If possible, measurements are made on the lower ADS before it is integrated in an absorbent article. If this is not possible, care should be exerted when excising the sample to not impart any contamination or distortion to the test sample layer during the removal the material from other layers (using cryogenic spray, such as Cyto-Freeze, Control Company, Houston, Texas, if needed). A rectangular material specimen 9 having a width of about 80 mm and a length of about 200 mm is cut from a roll stock of the nonwoven. The length corresponds to the longitudinal direction of the nonwoven web in the absorbent article and the width corresponds to the transverse direction of the nonwoven web in the absorbent article. The method can be alternatively conducted on a material specimen having a width of about 50 mm if the nonwoven original's width is shorter than 80 mm.

The material specimen 9 is laid flat on any suitable horizontal flat surface such as a lab bench, and a line is drawn at exactly at 100 mm from the front edge 8 of the material specimen in the width direction.

The material specimen 9 is then laid on top of the support box 2 with a first side of the specimen facing up (side A). The 100 mm line drawn is precisely positioned on the sharp edge 4 with the 100 mm long portion of the material specimen hanging free from the support box 2, as illustrated on FIG. 15. The section of the sample is held flush on the horizontal side of the sharp edge if needed.

The movable ruler 6 is positioned near the front edge 8 of the hanging specimen material so that the distance 7 of the hanging front edge 8 from the flat surface 5 can be measured. Since the hanging front edge 8 may not be perfectly horizontal, the distance is measured on the two corners of the hanging front edge 8, as well as in the center of the front edge 8, and the arithmetic mean of the three values recorded to the nearest mm.

The bending drop 1 is calculated as the difference between the exact Drape box height 3 (140 mm) and the recorded vertical distance 7 of the front edge 8 to the flat surface 5, as measured with the ruler 6 from the flat surface 5. The overall procedure above is repeated on five like material specimens. The arithmetic mean of the bending drop values for the five like material specimens is reported to the nearest mm as the Side A Horizontal Bending Drop at 100 mm.

The material specimen is then turned upside down (side B now up), and the same procedure described above is performed to obtain the Side B Horizontal Bending Drop. The Horizontal Bending Drop recorded overall for the material specimen is the greater of the side A Horizontal Bending Drop and the side B Horizontal Bending Drop.

Z-Compliance Index and Percent Recovery Measurement Method

Principle: This method measures the ability of a nonwoven web to be compressed in z-direction under applied pressure and then to recover to its original caliper after removing said applied pressure.

Setup: A vertically oriented electronic caliper tester having a precision of at least 0.01 mm with a 40 mm diameter circular foot may be used. The pressure exerted by the foot on the specimen is adjustable via the addition of pre-selected weights. Measurements are made at 0.85±0.05 kPa and 15.4±0.1 kPa.

Procedure: Measurements are performed at 23° C.±2° C. and 50%±2% RH. All samples should be kept at least 24 hours in these conditions to equilibrate before conducting the tests, unless indicated otherwise. If possible, measurements are made on the lower ADS before it is integrated in an absorbent article. If this is not possible, care should be exerted when excising the sample to not impart any contamination or distortion to the test sample layer during the removal the material from other layers (using cryogenic spray, such as Cyto-Freeze, Control Company, Houston, Texas, if needed). The lower ADS specimen is cut from to a square sample with a width of about 80 mm (or alternatively in case the material is not available in the suitable size in a material specimen with a width of about 50 mm).

The square sample specimen is positioned centered under the caliper foot and the caliper at 0.85±0.05 kPa (P1) is measured and recorded to the nearest 0.01 mm (C1). Without removing the sample from the equipment, the pressure is increased to 15.4±0.1 kPa (P2) and the caliper measured and recorded to the nearest 0.01 mm (C2). The pressure may be increased by adding a suitable weight on the caliper foot. Again without moving the sample, the exerted pressure is reduced back to 0.85±0.05 kPa (for example by removing the extra weight) and the caliper measured a third time (C3) and recorded to the nearest 0.01 mm.

For the specimen being measured, the compliance index is defined as:

Z-compliance index=(C1−C2)/(P2−P1)

and is recorded to the nearest 0.1 mm³/N.

The recovery is calculated as:

recovery=C3/C1*100% expressed in percent and recorded to the nearest 0.1%.

The procedure above is conducted on five like specimens of the same nonwoven. The arithmetic mean of the compliance index values among the five specimens is calculated and reported to the nearest 0.1 mm³/N as the Compliance Index. The arithmetic mean of percent recovery values among the five specimens is calculated and reported to the nearest 0.1% as the Percent Recovery.

In-Bag Stack Height

The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within +0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 gram.

Test Procedure

Absorbent article packages are equilibrated at 23±2° C. and 50±2% relative humidity prior to measurement.

Figure 14:
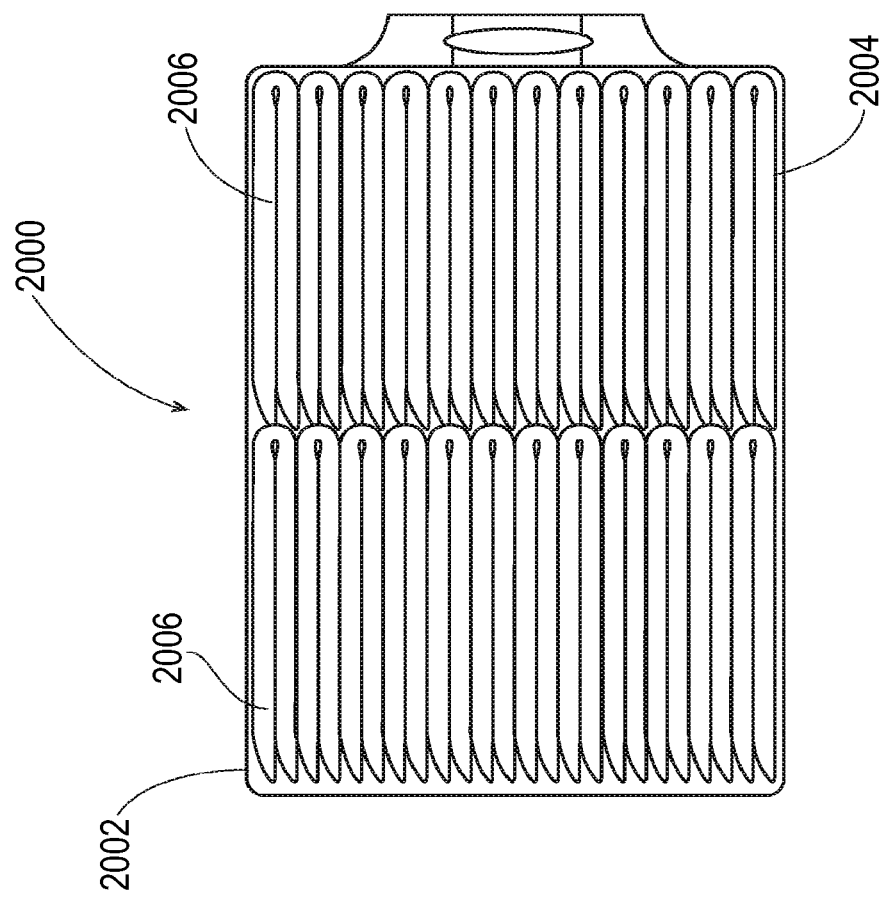
FIG. 14 is a package of the absorbent article of the present disclosure, wherein the article partially cut away to show of the package.

The horizontal sliding plate is raised and an absorbent article package is placed centrally under the horizontal sliding plate in such a way that the absorbent articles within the package are in a horizontal orientation (see FIG. 14). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within +0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within +0.5 mm.

Modified Fluid Acquisition Test

The Modified Fluid Acquisition ("MFA") Test is designed to measure the speed at which 0.9% saline solution is absorbed into an absorbent article that is compressed at 2.07 kPa. A known volume is introduced four times, each successive dose starting 300 seconds±5 seconds after the previous dose has absorbed. Times needed to absorb each dose are recorded. All testing is performed in a room maintained at about 23° C.±2 C.° and about 50%±2% relative humidity.

The test fluid is 0.9% w/v saline solution and is prepared by weighing 9.0 g±0.05 g of NaCl into a weigh boat, transferring it into a 1 L volumetric flask, and diluting to volume with de-ionized water.

The MFA apparatus is depicted in FIG. 19 through FIG. 12b. The MFA apparatus comprises a bladder assembly 3001 and a top plate assembly 3200 that includes a deposition assembly 3100. A controller 3005 is used to 1) monitor the impedance across electrodes 3106, recording the time interval 0.9% saline solution is in a cylinder 3102, 2) interface with a liquid pump 3004 to start/stop dispensing, and 3) time intervals between dosing. The controller 3005 is capable of recording time events to ±0.01 sec. A house air supply 3014 is connected to a pressure regulator 3006 capable of delivering air at a suitable flow/pressure to maintain 2.07 kPa in the bladder assembly 3001. A liquid pump 3004 (Ismatec MCP-Z gear pump, available from Cole Palmer, Vernon Hills, IL or equivalent) capable of delivering a flow of 10-80 mL at a rate of 3-15 mL/s is attached to a steel tube 3104 of the deposition assembly 3100 via tygon tubing 3015.

The bladder assembly 3001 is constructed of 12.7 mm Plexiglas with an overall dimension of 80 cm long by 30 cm wide by 10 cm tall. A manometer 3007 to measure the pressure inside the assembly and a pressure gauge 3006 to regulate the introduction of air into the assembly are installed through two holes through the right side. A bladder 3013 is assembled by draping a 50 mm by 100 mm piece of silicone film, (thickness 0.02", Shore A durometer value of 20, available as Part #86435K85 from McMaster-Carr, Cleveland, OH) over the top of the box with enough slack that the film touches the bottom of the box at its center point. An aluminum frame 3003 with a flange is fitted over the top of the film and secured in place using mechanical clamps 3010. When in place, the assembly should be leak free at a pressure of 3.45 kPa. A front 3008 and back 3009 sample support 5 cm by 30 cm by 1 mm are used to anchor the sample. The absorbent article is attached to the top surface of the sample supports by either adhesive tape or mechanical "hook" fasteners. These supports can be adjusted along the length of the aluminum frame 3003 via a simple pin and hole system to accommodate different size absorbent articles and to correctly align their loading point.

The top plate assembly 3200 is constructed of an 80 cm by 30 cm piece of 12.7 mm Plexiglas reinforced with an aluminum frame 3109 to enhance rigidity. The plate has a cutout 170 mm wide by 201 mm long centered laterally on the plate, 170 mm from the front of the plate 3201 for mounting of the deposition assembly. In addition, the top plate has thirty-six (36) 3.2 mm diameter holes drilled through it distributed as shown in FIG. 35A. The holes prevent air from being trapped under the top plate as the bladder is inflated. The top plate assembly 3200 is connected to the bladder assembly 3001 via two hinges 3012. During use, the top assembly is closed onto the bladder assembly and locked into place using a mechanical clamp 3011.

Figure 11B:
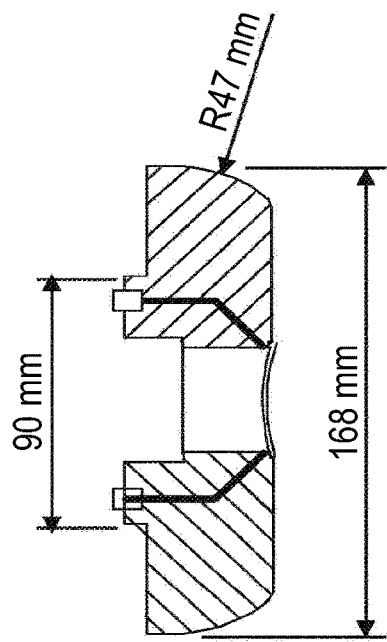
FIG. 11B is an end view of the curved component of FIG. 34A.
Figure 11E:
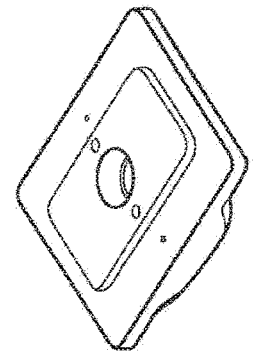
FIG. 11E is a top perspective view of the curved component of FIG. 34.
Figure 11D:
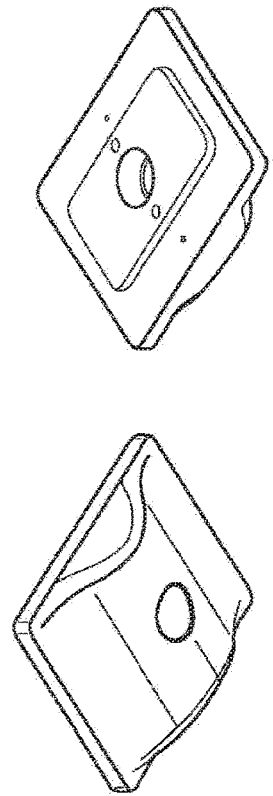
FIG. 11D is a bottom perspective view of the curved component of FIG. 34A.
Figure 11A:
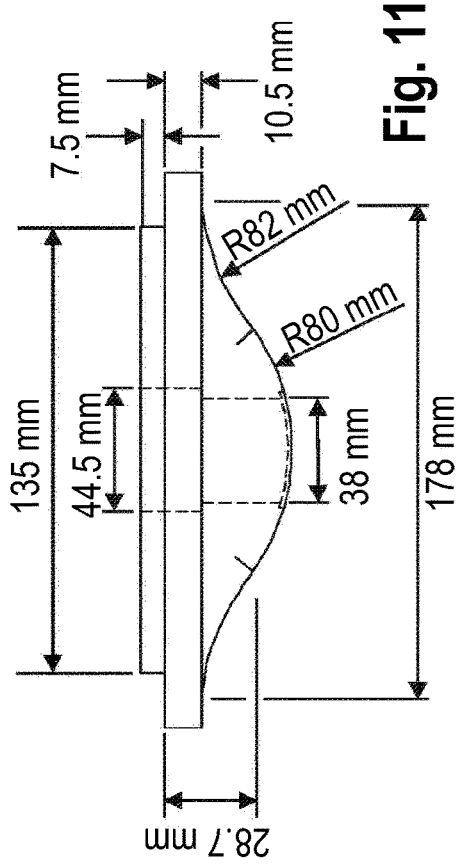
FIG. 11A is a side view of the curved component used in the Modified Fluid Acquisition Test.
Figure 11C:
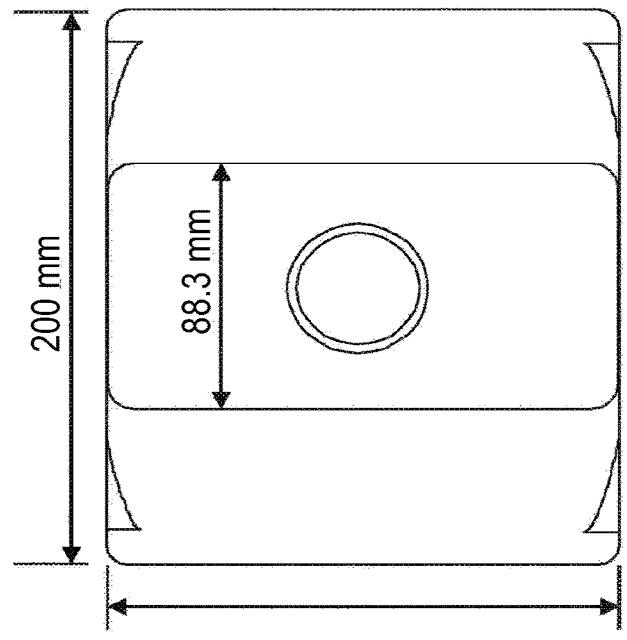
FIG. 11C is a bottom view of the curved component of FIG. 34A.

The deposition assembly 3100 is fitted into the top plate 3200 and includes 1) a liquid introduction cylinder 3102, 2) a curved surface 3101 at the loading point of the absorbent article and 3) electrodes 3106 that are used to detect fluid in the cylinder 3102. The detailed dimensions of the curved component are provided in FIG. 11A to FIG. 11E. FIG. 11A is a side view of the curved component. FIG. 11B is an end view of the curved component. FIG. 11C is a bottom view of the curved component. FIG. 11D is a bottom perspective view of the curved component. FIG. 11E is a top perspective view of the curved component. This curved component can be milled, or 3D printed. The top portion of the introduction cylinder is a 50.8 mm O.D. Plexiglas cylinder 3102 with a 38.1 mm I. D. This is fitted into the curved component to give the introduction cylinder a total height of 100 mm. Imbedded electrodes run from connectors on the upper surface of the curved component and terminate flush with an inside wall of the introduction cylinder, 2 mm from the bottom of the cylinder. The two electrodes are positioned 180 degrees apart. A nylon screen 3107 is cut and affixed flush with the bottom of the cylinder such that the sample cannot swell into the cylinder. A 5 mm semi-circle is cut in the screen in the immediate area of the two electrodes. The deposition assembly is inserted into the top plate as shown in FIG. 12A such that the curved surface is flush with the bottom of the top-plate assembly 3200. The introduction cylinder 3102 is topped with a loose-fitting nylon cap 3103. The cap has a 6.35 mm O.D. steel tube 3104 inserted through its center. When the cap is in place, the bottom of the tube ends 20 mm above the screen 3107. The cap also has an air hole 3105 to ensure negative pressure does not impede the absorption speed.

All sample articles are conditioned at 23° C.±2 C.° and about 50%±2% relative humidity for two hours prior to testing. The absorbent article is first prepared by excising any inner or outer leg cuffs, waist caps, elastic ears or side panels, taking care not to disturb the top sheet that resides above the article's core region. Place the absorbent article flat onto a lab bench and identify the intersection of the longitudinal centerline with the size dependent loading point.

Loading Points, Volumes, and Flow rate for Acquisition Testing are as follows:

For absorbent articles having a length of equal to or less than 450 mm (these are typically baby diapers of Size 0, 1 or 2, i.e. small sizes):
  Two gushes with 300 seconds±5 seconds waiting time between the end of the first gush and the start of the second gush.
  Each gush has a volume of 40 ml
  The loading point is at 138 mm from the end edge of the front waist region (i.e. the waist edge) of the absorbent article.
  The flow rate is 8 ml/s.

For absorbent articles having a length of 450 mm or larger:
  Two gushes with 300 seconds±5 seconds waiting time between the end of the first gush and the start of the second gush.
  Each gush has a volume of 75 ml
  The loading point is at 102 mm from the end edge of the front waist region (i.e. the waist edge) of the absorbent article.
  The flow rate is 15 ml/s.

The length of the absorbent article and the loading point (i.e. respective distance from the end edge of the front waist region of the absorbent article) are determined when the absorbent article is laid flat, with all elastics strands hindering a flattened out configuration (such as leg elastics) being cut and thus de-elasticized). The length is determined along the longitudinal centerline. Attach the front end of the absorbent article to the top surface of the front sample plate 3008 by either adhesive tape or mechanical "hook" fasteners with the top sheet facing upward. The placement is such that just the chassis and not the absorptive core overlays the plate. The sample plate 3008 is attached to the aluminum frame 3003 such that the size-dependent Loading Point (as defined in Table 2) of the absorbent article will be centered longitudinally and laterally within the cylinder 3102 when the top plate assembly has been closed. The back end of the absorbent article is secured to the back sample plate 3009 by either adhesive tape or mechanical "hook" fasteners, once again ensuring that only the chassis and not the absorptive core overlays the plate. The back sample plate 3009 is then attached to the aluminum frame 3003 such that the article is taunt but not stretched. The top plate assembly is closed and fastened, and the bladder is inflated to 2.07 kPa±0.07 kPa. The pressure is maintained at this level during the complete loading sequence of the test.

The pump 3004 is primed and then calibrated to deliver the size-dependent volume and flow rate selected from Table 2. Volume and flow rate must be within ±2% of target. The cap 3103 is placed into the cylinder 3102. The controller 3005 is started, which in turn delivers the first dose of 0.9% saline solution. After the volume has been absorbed, the controller waits for 5.0 minutes before addition of the next dose. This cycle is repeated for a total of four doses. If the fluid leaks out of or around the article (i.e., is not absorbed into the article) then the test is aborted. Also, if any acquisition time exceeds 1200 seconds, the test is aborted. The acquisition time is defined as the difference between the start time (i.e., when the 0.9% saline is first introduced into the cylinder and that conducting fluid completes the circuit between the electrodes) and the stop time (i.e., when the fluid has completely drained from the cylinder and the circuit between the electrodes is broken). Acquisition times are recorded by the controller for each dose to the nearest 1 second. After the last dose is acquired, pressure is applied for an additional 10 minutes. Open the pressure relief valve 3016 to deflate the bladder and then remove the sample from the acquisition system.

In like fashion, run a total of four (4) replicates for each absorbent article to be evaluated. Calculate and report the Acquisition Times (sec) for each dose as the arithmetic mean of the replicates to the nearest 1 sec.

EXAMPLES

A large number of materials for the lower ADS and several absorbent article configurations were tested. Moreover, a number of absorbent articles as currently available on the market were investigated as comparative examples for the present invention.

Comparative Examples

Commercially Available Baby Diapers

Pampers Cruisers™, US
Huggies Diamond™, US
Pampers Ichiban™, Japan
Baby Love™, purchased in Germany
Goo.N™, purchased in China
Merries™, purchased in China
Lelch™, purchased in China All tested products were taped diapers (i.e. not pants) as commercially available first half of 2019. While both Pampers diapers have an absorbent core that did not comprise any airfelt (all absorbent material are superabsorbent polymer particles), all other diapers had absorbent with superabsorbent polymer particles mixed with airfelt.

The diapers were subjected to the NMR MOUSE test to determine the amount of liquid in the first and second zone

TABLE 1

Comparative Examples, all Size 4; including data on the three NMR MOUSE measurement locations (at loading point, 4 cm and 8 cm away from loading point). The table lists the amounts of liquid in µl

| Zone | Measurement location - Distance from loading point towards back end | Pampers Cruisers | Huggies Diamond | Pampers Ichiban | Baby Love | Goo.N | Merries | Lelch |
|---|---|---|---|---|---|---|---|---|
| First zone | 0 cm | 28 | 58 | 24 | 29 | 95 | 34 | 72 |
| First zone | 4 cm | 18 | 22 | 14 | 14 | 20 | 10 | 37 |
| First zone | 8 cm | 17 | 26 | 15 | 12 | 21 | 11 | 33 |
| First zone | Sum of 0 cm, 4 cm and 8 cm | 63 | 106 | 53 | 55 | 136 | 55 | 142 |
| Second zone | 0 cm | 106 | 46 | 107 | 82 | 48 | 82 | 28 |
| Second zone | 4 cm | 59 | 35 | 60 | 62 | 23 | 63 | 24 |
| Second zone | 8 cm | 80 | 36 | 71 | 65 | 23 | 70 | 23 |
| Second zone | Sum of 0 cm, 4 cm and 8 cm | 244 | 117 | 238 | 209 | 94 | 215 | 75 |

TABLE 2

Comparative Examples, all Size 4; acquisition times

| Acquisition time | Goo.N | Lelch | Pampers Ichiban | Merries | Pampers Cruisers | Baby Love |
|---|---|---|---|---|---|---|
| $1^{st}$ gush time [s] | 79 | 75 | 44 | 60 | 69 | 60 |
| $2^{nd}$ gush time [s] | 266 | 353 | 59 | 188 | 80 | 62 |
| Total acquisition time [s] | 344 | 428 | 103 | 248 | 149 | 122 |

TABLE 3

Comparative Examples, all Size 2; including data on the three measurement locations (at loading point, 4 cm and 8 cm away from loading point). The table lists the amounts of liquid in µl.

| Zone | Measurement location - Distance from loading point towards back end | Goo.N | Merries | Lelch |
|---|---|---|---|---|
| First zone | 0 cm | 32 | 50 | 60 |
| First zone | 4 cm | 14 | 14 | 21 |
| First zone | 8 cm | 12 | 13 | 12 |
| First zone | Sum of 0 cm, 4 cm and 8 cm | 58 | 77 | 93 |
| Second zone | 0 cm | 85 | 62 | 29 |
| Second zone | 4 cm | 61 | 37 | 22 |
| Second zone | 8 cm | 31 | 25 | 11 |
| Second zone | Sum of 0 cm, 4 cm and 8 cm | 177 | 124 | 62 |

TABLE 4

Comparative Examples, all Size 2; acquisition time

| Acquisition time | Goo.N | Merries |
|---|---|---|
| 1st gush [s] | 38 | 45 |
| $2^{nd}$ gush [s] | 106 | 121 |
| Total ($1^{st}$ + $2^{nd}$ gush) [s] | 144 | 166 |

EXAMPLES OF THE INVENTION

A lower acquisition and distribution layer was added to some of the commercially available diapers above and the diapers were subjected to the NMR MOUSE test to determine the amount of liquid in the first and second zone.

The following materials were used as lower ADS, i.e. the material was added between the backsheet and the absorbent core:

Lower ADS option 1: Carded air through bonded nonwoven web made of 60 weight-% of CoPET/PET solid round bicomponent (core/sheath) staple fibers of 2.2 dtex and 40 weight-% of PET solid round monocomponent staple fibers of 3.3 dtex. The material had a basis weight of 30 g/m².

Lower ADS option 2: Carded air through bonded nonwoven web made of 100% polyethylene/PET solid round bicomponent (core/sheath) staple fibers of 4.4 dtex. The material had a basis weight of 60 g/m².

Lower ADS option 3: Air through bonded nonwoven web made of 60 weight % of CoPET/PET solid round bicomponent (core/sheath) staple fibers of 2.2 dtex and 40 weight-% of PET solid round monocomponent staple fibers of 3.3 dtex. The material had a basis weight of 60 g/m².

Lower ADS option 4: Hydroentangled nonwoven web with 30 weight-% viscose fibers and 70 weight-% polyester fibers. The nonwoven web had a basis weight of 40 g/m².

Lower ADS option 5: Nonwoven web made of 100% monocomponent PP with SMS layers. The spunbond ("S") layer has fibers of 2.2 dtex and the meltblown ("M") layer has fiber diameter lower than 2 microns. The meltblown layer has a basis weight of 1.8 g/m² and the spunbond layers each have a basis weight of 9.1 g/m². The nonwoven web had a basis weight of 20 g/m².

Lower ADS option 6: Spunbonded nonwoven web, made of crimped PP/PP fibers. The nonwoven is hydroentangled. The web had a basis weight of 35 g/m².

Examples, Size 4

Sample Preparation:

For the modified Pampers Cruisers (Size 4): The topsheet, upper ADS and absorbent core (i.e. the layer of absorbent material enclosed by an upper and a lower substrate layer) of the Pampers Cruisers diaper, Size 4, as commercially available in the USA in the first half of 2019 were removed carefully using ice-spray. The original absorbent core was carefully kept aside and the original topsheet and upper ADS were disposed. For each diaper, the lower ADS was attached to the wearer-facing surface of the backsheet with a hot melt adhesive applied in form of spirals with a basis weight of 5 g/m$^2$. The lower ADS had a width of 90 mm and was centered on the backsheet with respect to the transverse direction. The lower ADS had the same length as the original absorbent core and was placed at the same position as the original absorbent core with respect to the longitudinal direction. The original absorbent core was then attached to the lower ADS with a hot melt adhesive applied in form of spirals with a basis weight of 5 g/m$^2$ such that the absorbent core was placed in the exact position as before removal. In other words, the front edge of the lower ADS corresponded with the front edge of the absorbent core. An upper ADS having a length of 360 mm was then attached to the absorbent core with a hot melt adhesive applied in form of spirals with a basis weight of 5 g/m$^2$ such that the upper ADS was centered on the absorbent core with respect to the transverse direction and spaced 18 mm from the absorbent core front edge, towards the back with respect to the longitudinal direction. The upper ADS comprised an upper layer having a width of 90 mm and made of air-through bonded nonwoven web, made of a mixture of 60 weight % of CoPET/PET solid round bicomponent (core/sheath) staple fibers of 2.2 dtex and 40 weight % of PET solid round monocomponent staple fibers of 3.3 dtex. The upper layer of the upper ADS had a basis weight of 30 g/m$^2$. The upper ADS further comprised a lower layer having a width of 80 mm and made of crosslinked cellulose fibers. The lower layer of the upper ADS had a basis weight of 170 g/m$^2$. Both layers of the upper ADS were attached to each other with a hot melt adhesive applied in form of stripes with a basis weight of 5 g/m$^2$. The upper and lower layer of the upper ADS were centered on each other with respect to the transverse direction and such that the front edges of the upper and lower layer of the upper ADS were matching.

Finally, a spunbonded nonwoven web made on a forming belt as described in WO 2017/105997A1 was attached to the upper ADS as a topsheet with a hot melt adhesive applied in form of spirals with a basis weight of 5 g/m$^2$. The nonwoven web forming the topsheet comprised continuous bicomponent polypropylene/polypropylene (side-by-side) fibers and had a basis weight of 25 g/m$^2$. Due to the formation on a forming belt, the nonwoven web had regions of higher and lower basis weight.

The diaper samples were compacted in a flexible bag at an In Bag Stack Height, i.e. the total caliper of 10 bi-folded diapers, of 85 mm for 1 week. Then the bag was opened and the diapers out of the bag were conditioned at least 24 hours prior to any testing at 23° C.+/−2° C. and 50%+/−10% Relative Humidity (RH).

For the modified Merries (Size 4): The commercial topsheet, upper ADS and absorbent core (i.e. the layer of absorbent material wrapped in an upper and a lower substrate layer) of the Merries diaper, Size 4, as commercially available in Japan in the first half of 2019 were removed carefully as one laminate using ice-spray. For each diaper, the lower ADS was attached to the wearer-facing surface of the backsheet with a hot melt adhesive applied in form of spirals with a basis weight of 5 g/m$^2$. The lower ADS had a width of 90 mm and was centered on the backsheet with respect to the transverse direction. The lower ADS had the same length as the original absorbent core and was placed at the same position as the original absorbent core with respect to the longitudinal direction. The laminate formed by the original absorbent core, upper ADS and topsheet was then attached to the lower ADS with a hot melt adhesive applied in form of spirals with a basis weight of 5 g/m$^2$ such that the absorbent core was placed in the exact position as before removal. In other words, the front edge of the lower ADS corresponded with the front edge of the absorbent core. The diaper samples were compacted in a flexible bag at an In Bag Stack Height, i.e. the total caliper of 10 bi-folded diapers, of 90 mm for 1 week. Then the bag was opened and the diapers out of the bag were conditioned at least 24 hours prior to any testing at 23° C.+/−2° C. and 50%+/−10% Relative Humidity (RH).

For the modified Pampers Ichiban (Size 4): The commercial topsheet, upper ADS and absorbent core (i.e. the layer of absorbent material wrapped in an upper and a lower substrate layer) of the Pampers Ichiban diapers, Size 4, commercially available in China in the first half of 2019 were removed carefully using ice-spray. The original absorbent core was carefully kept aside and the original topsheet and upper ADS were disposed. For each diaper, the lower ADS was attached to the wearer-facing surface of the backsheet with a hot melt adhesive applied in form of spirals with a basis weight of 5 g/m$^2$. The lower ADS had a width of 90 mm and was centered on the backsheet with respect to the transverse direction. The lower ADS had the same length as the original absorbent core and was placed at the same position as the original absorbent core with respect to the longitudinal direction. The original absorbent core was then attached to the lower ADS with a hot melt adhesive applied in form of spirals with a basis weight of 5 g/m$^2$ such that the absorbent core was placed in the exact position as before removal. In other words, the front edge of the lower ADS corresponded with the front edge of the absorbent core. An upper ADS having a length of 360 mm was then attached to the absorbent core with a hot melt adhesive applied in form of spirals with a basis weight of 5 g/m$^2$ such that the upper ADS was centered on the absorbent core with respect to the transverse direction and spaced 18 mm away from the absorbent core front edge with respect to the longitudinal direction. The upper ADS comprised an upper layer having a width of 90 mm and made of air-through bonded nonwoven web, made of 60 weight-% of CoPET/PET solid round bicomponent (core/sheath) staple fibers of 2.2 dtex and 40 weight-% of PET solid round monocomponent staple fibers of 3.3 dtex. The upper layer of the upper ADS had a basis weight of 30 g/m$^2$. The upper ADS also comprised a lower layer having a width of 80 mm and made of crosslinked cellulose fibers. The lower layer of the upper ADS had a basis weight of 170 g/m$^2$. Both layers of the upper ADS were attached to each other with a hot melt adhesive applied in form of stripes with a basis weight of 5 g/m$^2$. The upper and lower layer of the upper ADS were centered on each other with respect to the transverse direction and such that the front edges of the upper and lower layer of the upper ADS were matching.

Finally, a spunbonded nonwoven web made on a forming belt as described in WO 2017/105997A1 was attached to the upper ADS as a topsheet with a hot melt adhesive applied in form of spirals with a basis weight of 5 g/m$^2$. The nonwoven web of the topsheet comprised bicomponent continuous polypropylene/polypropylene (side-by-side) fibers and had a basis weight of 25 g/m$^2$. Due to the formation on a forming belt, the nonwoven web had regions of higher and lower basis weight.

The diaper samples were compacted in a flexible bag at an In Bag Stack Height, i.e. the total caliper of 10 bi-folded diapers, of 90 mm for 1 week. Then the bag was opened and the diapers out of the bag were conditioned at least 24 hours prior to any testing at 23° C.+/−2° C. and 50%+/−10% Relative Humidity (RH).

TABLE 5

Size 4 diapers with lower ADS. The table lists the amounts of liquid in μl.

| Zone | Measurement location - Distance from loading point towards back end | Modified Merries with lower ADS option 1 | Modified Merries with lower ADS option 2 | Modified Pampers Ichiban lower ADS option 2 | Modified Pampers Cruisers with lower ADS option 1 | Modified Pampers Cruisers with lower ADS option 3 |
|---|---|---|---|---|---|---|
| First zone | 0 cm | 37 | 48 | 14 | 17 | 16 |
| First zone | 4 cm | 12 | 19 | 12 | 12 | 13 |
| First zone | 8 cm | 10 | 15 | 12 | 11 | 13 |
| First zone | Sum of 0 cm, 4 cm and 8 cm | 59 | 82 | 39 | 40 | 42 |
| Second zone | 0 cm | 31 | 16 | 18 | 45 | 22 |
| Second zone | 4 cm | 20 | 12 | 12 | 13 | 10 |
| Second zone | 8 cm | 24 | 11 | 9 | 12 | 12 |
| Second zone | Sum of 0 cm, 4 cm and 8 cm | 76 | 38 | 39 | 70 | 44 |

Examples, Size 2

Modified Pampers Ichiban, Size 2; Execution 1: The commercial topsheet, upper ADS and absorbent core of the Pampers Ichiban diaper, Size 2, commercially available in China in the first half of 2019 were removed carefully using ice-spray. The original absorbent core was carefully kept aside and the original topsheet and upper ADS were disposed. For each diaper, the lower ADS was attached to the wearer-facing surface of the backsheet with a hot melt adhesive applied in form of spirals with a basis weight of 5 g/m². The lower ADS had a width of 90 mm and was centered on the backsheet with respect to the transverse direction. The lower ADS had the same length as the original absorbent core and was placed at the same position of the original absorbent core with respect to the longitudinal direction. The original absorbent core was then attached to the lower ADS with a hot melt adhesive applied in form of spirals with a basis weight of 5 g/m² such that the absorbent core was placed in the exact position as before removal. In other words, the front edge of the lower ADS corresponded with the front edge of the absorbent core. An upper ADS having a length of 350 mm was then attached to the absorbent core with a hot melt adhesive applied in form of spirals with a basis weight of 5 g/m² such that the upper ADS was centered on the absorbent core with respect to the transverse direction and spaced 23 mm from the front end edge of the absorbent article with respect to the longitudinal direction. The upper ADS comprised an upper layer having a width of 90 mm and made of air-through bonded nonwoven web, made of 60 weight-% of CoPET/PET solid round bicomponent (core/sheath) staple fibers of 2.2 dtex and 40 weight-% of PET solid round monocomponent staple fibers of 3.3 dtex. The upper layer of the upper ADS had a basis weight of 30 g/m². The upper ADS also comprised a lower layer having a width of 80 mm and made of crosslinked cellulose fiber. The lower layer of the upper ADS had a basis weight of 110 g/m². The upper and lower layer of the upper ADS were attached to each other with a hot melt adhesive applied in form of stripes with a basis weight of 5 g/m². The upper and lower layer of the upper ADS were centered on each other with respect to the transverse direction and such that the front edges of the upper and lower layer of the upper ADS were matching.

Finally, a spunbonded nonwoven web with monocomponent polypropylene fibers was attached to the upper ADS as a topsheet with a hot melt adhesive applied in form of spirals with a basis weight of 5 g/m². The nonwoven web of the topsheet had a basis weight of 12 g/m². The diaper samples were compacted in a bag at an In Bag Stack Height, i.e. the total caliper of 10 bi-folded diapers, of 100 mm for 1 week. Then the bag was opened and the diapers out of the bag were conditioned at least 24 hours prior to any testing at 23° C.+/−2° C. and 50%+/−10% Relative Humidity (RH).

Modified Pampers Ichiban, Size 2; Execution 2: For Execution 2, the same procedure was followed as set out above for Execution 1, except that the materials of the upper ADS were different. The upper ADS of Execution 2 was a bilayer material, wherein the upper layer of the upper ADS in direct contact with the topsheet was a carded, air-through bonded nonwoven web of polyethylene/polypropylene bicomponent fibers and having a basis weight of 20 g/m². The lower layer of the upper ADS in direct contact with the upper substrate layer of the absorbent core was a 60 g/m² nonwoven web made of 3 weight-% latex, 20 weight-% polypropylene/PET bicomponent fibers and 77 weight-% of cellulose fibers. The upper ADS had a total basis weight of 80 g/m².

Comparative Example I without lower ADS: modified Pampers Ichiban, Size 2 The commercial topsheet and upper ADS of the Pampers Ichiban diaper, Size 2, as commercially available in China in the first half of 2019, were removed carefully using ice-spray and the original topsheet and upper ADS were disposed. An upper ADS having a length of 350 mm was then attached to the absorbent core with a hot melt adhesive applied in form of spirals with a basis weight of 5 g/m² such that the upper ADS was centered on the absorbent core with respect to the transverse direction and spaced 23 mm away from the front end edge of the absorbent article with respect to the longitudinal direction. The upper ADS comprised an upper layer having a width of 90 mm and which was made of the same material as the one used as option 1 of the lower ADS in other examples herein. The upper ADS also comprised a lower layer having a width of 80 mm and made of crosslinked cellulose fiber. The lower layer of the upper ADS had a basis weight of 140 g/m². The upper and lower layer of the upper ADS were attached to each other with a hot melt adhesive applied in form of stripes with a basis weight of 5 g/m². The upper and lower layer of the upper ADS were centered on each other with respect to the transverse direction and such that the front edges of the upper and lower layer of the upper ADS were matching.

Finally, a spunbonded nonwoven web with monocomponent polypropylene fibers was attached to the upper ADS as a topsheet with a hot melt adhesive applied in form of spirals with a basis weight of 5 g/m². The nonwoven web of the topsheet had a basis weight of 12 g/m². The diaper samples were compacted in a bag at an In Bag Stack Height, i.e. the total caliper of 10 bi-folded diapers, of 100 mm for 1 week. Then the bag was opened and the diapers out of the bag were conditioned at least 24 hours prior to any testing at 23° C.+/−2° C. and 50%+/−10% Relative Humidity (RH).

Comparative Example II without lower ADS: modified Pampers Ichiban, Size 2: The upper layer of the upper ADS was an air-through bonded nonwoven web with 30 g/m² basis weight, made of 60 weight-% of CoPET/PET solid round bicomponent (core/sheath) staple fibers of 2.2 dtex and 40 weight-% of PET solid round monocomponent staple fibers of 3.3 dtex. The lower layer of the upper ADS was made of crosslinked cellulose fiber and having a basis weight of 110 g/m². A spunbonded nonwoven web having a basis weight of 12 g/m² and made of monocomponent polypropylene fibers was used as topsheet.

All other sample preparation steps, dimensions and configuration of the samples was identical to Comparative Example I described above.

Comparative Example III without lower ADS: modified Pampers Swaddlers, Size 2. The product design of this example is similar to the Pampers Swaddlers diaper, Size 2, commercially available in North America in the first half of 2019 with the following changes described below. The absorbent material or super-absorber was 6.6 grams in weight and followed the same distribution as market product. The upper layer of the upper ADS was made with the same material of the one used in the market product, with a length of 288 mm and a width of 105 mm. The upper layer of the upper ADS was placed 31 mm away from the front end edge of the absorbent core. The lower layer of the upper ADS was made of the same material used in the market product, with a length of 268 mm and a width of 80 mm. The lower layer of the upper ADS was placed 10 mm away from the front end edge of the upper layer of the upper ADS. The backsheet is made of a spunlaid hydroentangled web of 30 g/m² that is attached to the backsheet film with a hot melt adhesive applied in form of slots with a basis weight of 5 g/m².

The diaper samples were compacted in a bag at an In Bag Stack Height, i.e. the total caliper of 10 bi-folded diapers, of 100 mm for 1 week. Then the bag was opened and the diapers out of the bag were conditioned at least 24 hours prior to any testing at 23° C.+/−2° C. and 50%+/−10% Relative Humidity (RH).

TABLE 6

Modified Pampers Ichiban, Size 2, with lower ADS. The table lists the amounts of liquid in µl.

| Zone | Measurement location - Distance from loading point towards back end | Execution 1 with lower ADS option 1 | Execution 1 with lower ADS option 2 | Execution 1 with lower ADS option 4 | Execution 1 with lower ADS option 5 | Execution 2 with lower ADS option 1 | Execution 2 with lower ADS option 2 | Comparative Example I |
|---|---|---|---|---|---|---|---|---|
| First zone | 0 cm | 19 | 19 | 19 | 17 | 41 | 39 | 17 |
| First zone | 4 cm | 12 | 13 | 12 | 11 | 29 | 23 | 11 |
| First zone | 8 cm | 12 | 13 | 8 | 10 | 15 | 13 | 11 |
| First zone | Sum of 0 cm, 4 cm and 8 cm | 42 | 44 | 39 | 38 | 85 | 75 | 39 |
| Second zone | 0 cm | 30 | 11 | 23 | 36 | 33 | 17 | 91 |
| Second zone | 4 cm | 14 | 13 | 10 | 17 | 15 | 10 | 55 |
| Second zone | 8 cm | 18 | 13 | 10 | 14 | 13 | 8 | 56 |
| Second zone | Sum of 0 cm, 4 cm and 8 cm | 62 | 37 | 43 | 67 | 61 | 35 | 203 |

TABLE 7 modified Pampers Ichiban, Size 2, with lower ADS. Acquisition times

| Acquisition Time | Execution 1 with lower ADS option 1 | Execution 1 with lower ADS option 2 | Execution 1 with lower ADS option 4 | Execution 1 with lower ADS option 5 | Comparative Example I | Comparative Example II |
|---|---|---|---|---|---|---|
| 1st gush time [s] | 31 | 34 | 31 | 31 | 27 | 38 |
| 2nd gush time [s] | 41 | 47 | 59 | 49 | 40 | 48 |
| Total acquisition time [s] | 72 | 81 | 90 | 80 | 67 | 86 |

Examples With and Without Lower Substrate Layer Below the Layer of Absorbent Material To compare absorbent articles wherein a lower substrate layer is provided between the layer of absorbent material and the lower ADS (as is the case in all inventive examples above) with absorbent articles wherein the lower ADS is in direct contact with the garment-facing surface of the layer of absorbent material, one of the embodiments above (Pampers Ichiban, Size 2, Execution 1 with lower ADS option 2) was modified such that the lower substrate layer was removed. The results are shown in Table 8. Another example was made replacing the lower substrate layer of Comparative Example III by the lower ADS option 6.

TABLE 8

Comparison between diaper with and without lower substrate layer on Size 2 diapers. The table lists the amounts of liquid in μl.

| Zone | | Execution 1 with lower ADS option 2 | Execution 1 with lower ADS option 2 but lower substrate layer removed | Comparative Example III with lower ADS option 6 and lower substrate layer removed | Comparative Example III without lower ADS |
|---|---|---|---|---|---|
| 1st Zone | 0 cm | 19 | 24 | 19 | 18 |
| $1^{st}$ Zone | 4 cm | 13 | 10 | 12 | 14 |
| $1^{st}$ Zone | 8 cm | 13 | 9 | 13 | 13 |
| $1^{st}$ Zone | Sum of 0 cm, 4 cm and 8 cm | 44 | 43 | 44 | 45 |
| $2^{nd}$ zone | 0 cm | 11 | 12 | 39 | 62 |
| $2^{nd}$ zone | 4 cm | 13 | 9 | 10 | 32 |
| $2^{nd}$ Zone | 8 cm | 13 | 10 | 10 | 33 |
| $2^{nd}$ zone | Sum of 0 cm, 4 cm and 8 cm | 37 | 31 | 59 | 127 |

TABLE 9

Table showing nonwoven webs suitable for use as lower ADS

| Material | Basis weight [g/m²] | Dry Opacity [%] | Airperm. [m³/m²/min] | Horizontal Bending Drop at 100 mm [mm] | Percentage Recovery [%] | Z-Compliance Index | Caliper [2.1 kPA/0.3 psi] |
|---|---|---|---|---|---|---|---|
| lower ADS option 2 | 60 | 66 | 269 | 66 | 59.1 | 31.8 | 0.44 |
| Carded air through bonded nonwoven web made of 60 weight-% of CoPET/PET solid round bicomponent (core/sheath) staple fibers of 2.2 dtex and 40 weight-% of PET solid round mono-component staple fibers of 3.3 dtex. | 45 | 34 | 342 | 75 | 82.7 | 13.4 | 0.33 |
| lower ADS option 1 | 30 | 27 | 485 | 92 | 75.1 | 11.7 | 0.28 |
| Carded air through bonded nonwoven web made of 100% bicomponent PE/PET (core sheath) fibers of 2.2 dtex. | 20 | 36 | 489 | 89 | 65 | 9.6 | 0.12 |
| Spunlace with 20 weight % of Viscose and 80 weight % of mono-component PET fibers | 40 | 52 | 236 | n.a | n.a | n.a | 0.34 |
| Carded calendar bonded material made of 2 layers. Layer one is made of 70 weight % PET fibers of 6.7 dtex and 30 weight % PP fibers of 2.2 dtex (30 g/m²). Layer 2 is made of 100 weight % of PP fibers | 40 | 33 | 310 | 92 | 58.5 | 30 | 0.42 |
| 24 gsm Highloft SSS (i.e. 3 spunbond layers) Spunlaid with crimped bicomponent PP/PP fibers | 24 | 36 | 252 | 97 | 74.6 | 7.1 | 0.17 |
| Lower ADS option 5 | 20 | 29 | 172 | 93 | 83 | 4.3 | 0.11 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. Absorbent article comprising:
  a topsheet, a backsheet, and a layer of absorbent material interposed between the topsheet and the backsheet, wherein the layer of absorbent material comprises superabsorbent polymer; and a lower acquisition and distribution system with at least one nonwoven or woven layer, the lower acquisition and distribution system being interposed between the layer of absorbent material and the backsheet;

wherein the absorbent article has a first zone corresponding to about 800 μm starting from and including the topsheet and extending towards the backsheet, and a second zone corresponding to about 800 μm starting from and including the backsheet and extending towards the topsheet; and wherein the absorbent article has a total amount of liquid of less than about 90 μl in the first zone and a total amount of liquid of less than about 80 μl in the second zone, upon being subjected to the NMR MOUSE test method set out herein, determining and adding up the amount of liquid in three defined locations.

2. The absorbent article of claim 1, wherein the amount of liquid at the loading point in the second zone as measured by the NMR MOUSE test method set out herein, is not more than about 50 μl.

3. The absorbent article of claim 1, the amount of liquid at the loading point in the first zone as measured by the NMR MOUSE test method set out herein, is not more than about 50 μl.

4. The absorbent article of claim 1, comprising an upper acquisition and distribution system with at least one layer, the upper acquisition and distribution system being interposed between the layer of absorbent material and the topsheet.

5. The absorbent article of claim 1, wherein the nonwoven comprised by the lower acquisition and distribution system is a nonwoven web selected from the group consisting of an air-through bonded nonwoven made of staple fibers, a spunlace nonwoven made of staple fibers, an air-through bonded nonwoven made of spunlaid fibers and a spunlace nonwoven made of spunlaid fibers.

6. The absorbent article of claim 1, wherein the fibers of the nonwoven comprised by the lower acquisition and distribution layer, comprise at least about 30 weight %, of crimped fibers based on the total weight of the nonwoven comprised by the lower acquisition and distribution layer, and wherein the crimped fibers have two-dimensional crimp, three dimensional crimp or a combination of two-and three-dimensional crimp.

7. The absorbent article of claim 1, wherein the nonwoven comprised by the lower acquisition and distribution system is made of polyethylene terephthalate (PET), co-PET, polypropylene, polyethylene, polylactic acid (PLA), polyhydroxy alkanoid (PHA), or combinations or mixtures thereof.

8. The absorbent article of claim 1, wherein the lower acquisition and distribution system has an air permeability greater than about 150 m$^3$/m$^2$/min.

9. The absorbent article of claim 1, wherein the absorbent article has a total acquisition time of less than about 120 seconds, as measured according to the test method set out herein.

10. The absorbent article of claim 1, wherein the caliper of the lower acquisition and distribution system is from about 0.1 to about 2.0 mm.

11. The absorbent article of claim 1, wherein portions or all of the lower acquisition and distribution system are mechanically deformed.

12. The absorbent article of claim 1, wherein the lower acquisition and distribution system consists of a single layer of a nonwoven web.

13. The absorbent article of claim 4, wherein the layer of absorbent material is partly or fully enclosed by and in direct contact with an upper and a lower substrate layer, wherein the upper substrate layer is between the layer of absorbent material and the upper acquisition and distribution system, and wherein the lower substrate layer is between the layer of absorbent material and the lower acquisition and distribution system.

14. The absorbent article of claim 13, wherein the lower acquisition and distribution system and the lower substrate layer are selected from the group consisting of a) the lower acquisition and distribution system is hydrophobic and the lower substrate layer is hydrophilic, b) the lower acquisition and distribution system and the lower substrate layer are both hydrophilic and the lower acquisition and distribution system is less hydrophilic than the lower substrate layer; and c) the lower acquisition and distribution system and the lower substrate layer are both hydrophobic and the lower substrate layer is less hydrophobic than the lower acquisition and distribution system.

15. The absorbent article of claim 13, wherein the layer of absorbent material and the lower acquisition and distribution system are partly or fully enclosed by and in direct contact with an upper and a lower substrate layer, wherein the upper substrate layer is between the layer of absorbent material and the upper acquisition and distribution system, and the lower substrate layer is between the lower acquisition and distribution system and the backsheet, and wherein the layer of absorbent material is in direct contact with the lower acquisition and distribution system.

16. The absorbent article of claim 13, wherein the layer of absorbent material is partly or fully enclosed by and in direct contact with an upper substrate layer and the lower acquisition and distribution system, and wherein the upper substrate layer is between the layer of absorbent material and the upper acquisition and distribution system.

17. The absorbent article of claim 1, wherein the wearer- and/or garment-facing surfaces of the lower acquisition and distribution system have a three-dimensional surface topography, and wherein the layers, which are adjacent to the surface having three-dimensional surface topography, have a flat, two-dimensional surface topography.

18. The absorbent article of claim 1, wherein the backsheet is breathable.

19. The absorbent article of claim 1, wherein the absorbent article has a length of more than about 450 mm.

20. The absorbent article of claim 18, wherein the absorbent article has a length of equal to or less than about 450 mm.

21. The absorbent article of claim 1, wherein the lower acquisition and distribution system has a Compliance Index greater than about 4.

22. The absorbent article of claim 1, wherein the lower acquisition and distribution system has an Horizontal Bending Drop greater than about 60.

23. The absorbent article of claim 1, wherein the lower acquisition and distribution system has a Percentage Recovery greater than about 50.

* * * * *